United States Patent
Buie et al.

(10) Patent No.: US 10,947,526 B2
(45) Date of Patent: Mar. 16, 2021

(54) MICROFLUIDIC ASSAY FOR RAPID OPTIMIZATION OF CELL ELECTROPORATION

(71) Applicant: Massachusetts Institute of Technology, Cambridge, MA (US)

(72) Inventors: Cullen Richard Buie, Cambridge, MA (US); Paulo Andres Garcia Dominguez, Cambridge, MA (US); Zhifei Ge, Cambridge, MA (US); Jeffrey Lawrence Moran, Boston, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 245 days.

(21) Appl. No.: 15/320,696

(22) PCT Filed: Dec. 10, 2014

(86) PCT No.: PCT/US2014/069615
§ 371 (c)(1),
(2) Date: Dec. 20, 2016

(87) PCT Pub. No.: WO2016/003485
PCT Pub. Date: Jan. 7, 2016

(65) Prior Publication Data
US 2017/0218355 A1      Aug. 3, 2017

Related U.S. Application Data

(60) Provisional application No. 62/020,959, filed on Jul. 3, 2014.

(51) Int. Cl.
*C12N 13/00*     (2006.01)
*C12M 3/06*      (2006.01)
(Continued)

(52) U.S. Cl.
CPC .......... *C12N 13/00* (2013.01); *B01L 3/50273* (2013.01); *B01L 3/502715* (2013.01);
(Continued)

(58) Field of Classification Search
CPC .............................. C12M 23/16; C12M 35/02
See application file for complete search history.

(56) References Cited

U.S. PATENT DOCUMENTS 7,678,564 B2    3/2010   Muller-Hartmann et al.
9,039,883 B2    5/2015   Guerrieri et al.
(Continued)

FOREIGN PATENT DOCUMENTS

EP       1 329 502           7/2003
WO    WO 2006/001614 A1     1/2006
(Continued)

OTHER PUBLICATIONS

Andresen et al. "Injection molded chips with integrated conducting polymer electrodes for electroporation of cells." J. Micromech. Microeng. vol. 20 (2010), pp. 1-9. (Year: 2010).*
(Continued)

*Primary Examiner* — William H. Beisner
(74) *Attorney, Agent, or Firm* — Hamilton, Brook, Smith & Reynolds, P.C.

(57) ABSTRACT

An electroporation device with a volume of varying cross sectional area that as a fast assay device for determining the optimal conditions for plasma membrane electroporation.

9 Claims, 25 Drawing Sheets

(51) Int. Cl.
*C12M 1/42* (2006.01)
*C12M 1/26* (2006.01)
*B01L 3/00* (2006.01)

(52) U.S. Cl.
CPC ....... *B01L 3/502761* (2013.01); *C12M 23/16* (2013.01); *C12M 33/00* (2013.01); *C12M 35/02* (2013.01); *B01L 2200/10* (2013.01); *B01L 2300/0645* (2013.01); *B01L 2300/0877* (2013.01); *B01L 2300/12* (2013.01)

(56) References Cited

U.S. PATENT DOCUMENTS

| | | | |
|---|---|---|---|
| 10,376,889 | B1 | 8/2019 | Masquelier et al. |
| 10,415,058 | B2 | 9/2019 | Bernate et al. |
| 10,450,543 | B2 | 10/2019 | Chang et al. |
| 2005/0048651 | A1 | 3/2005 | Ryttsen et al. |
| 2006/0115888 | A1 | 6/2006 | Gamelin et al. |
| 2007/0105206 | A1 | 5/2007 | Lu et al. |
| 2018/0179485 | A1 | 6/2018 | Borenstein et al. |
| 2019/0136224 | A1 | 5/2019 | Garcia Dominguez et al. |

FOREIGN PATENT DOCUMENTS

| | | |
|---|---|---|
| WO | WO 2006/004558 A1 | 1/2006 |
| WO | WO 2006/112870 | 10/2006 |
| WO | WO 2009/129327 A1 | 10/2009 |
| WO | WO 2013/059343 A1 | 4/2013 |
| WO | WO 2016/003485 A1 | 1/2016 |
| WO | WO 2017/210334 A1 | 12/2017 |

OTHER PUBLICATIONS

Kim et al. "Cell electroporation chip using multiple electric fields zones in a single channel." Applied Physics Letters, vol. 101 (2012), pp. 223705-1-223705-5. (Year: 2012).*

International Preliminary Report on Patentability, issued in International Application No. PCT/US2014/069615, entitled "Microfluidic Assay for Rapid Optimization of Cell Electroporation," 8 pages; dated Jan. 12, 2017.

Garcia, P.A., et al., "Intracranial Nonthermal Irreversible Electroporation: In Vivo Analysis," *J. Membrane Biol.*, 236:127-136 (2010).

Geng, T. et al., "Microfluidic Electroporation for Cellular Analysis and Delivery," *Lab Chip*, 13:3803-3821 (2013).

Geng, T. et al., "Transfection of Cells Using Flow-Through Electroporation based on Constant Voltage," *Nature Protocols*, 6(8):1192-1208 (2011).

Wang, H-Y., et al., "A Microfluidic Flow-Through Device for High Throughput Electrical Lysis of Bacterial Cells Based on Continuous DC voltage," *Biosensors and Bioelectronics*, 22:582-588 (2006).

Gallo-Villanueva, R.C., et al., "Joule Heating Effects on Particle Immobilization in Insulator-Based Dielectrophoretic Devices," *Eelectrophoresis*, 35(0):352-361 (2014).

Notification of Transmittal of the International Search Report and the Written Opinion of the International Searching Authority dated Aug. 28, 2017 for International Application No. PCT/US2017/035270, entitled "Hydrodynamically Controlled Electric Fields For High Throughput Transformation & High Throughput Parallel Transformation Platform," 15 pgs.

Notification of Transmittal of the International Search Report and the Written Opinion of the International Searching Authority from International Application No. PCT/US2014/069615, dated Dec. 16, 2015; Entitled: "Microfluidic Assay for Rapid Optimization of Cell Electroporation".

International Preliminary Report on Patentability for International Application No. PCT/US2017/035270, titled, "Hydrodynamically Controlled Electric Fields for High Throughput Transformation & High Throughput Parallel Transformation Platform", dated Dec. 4, 2018.

* cited by examiner

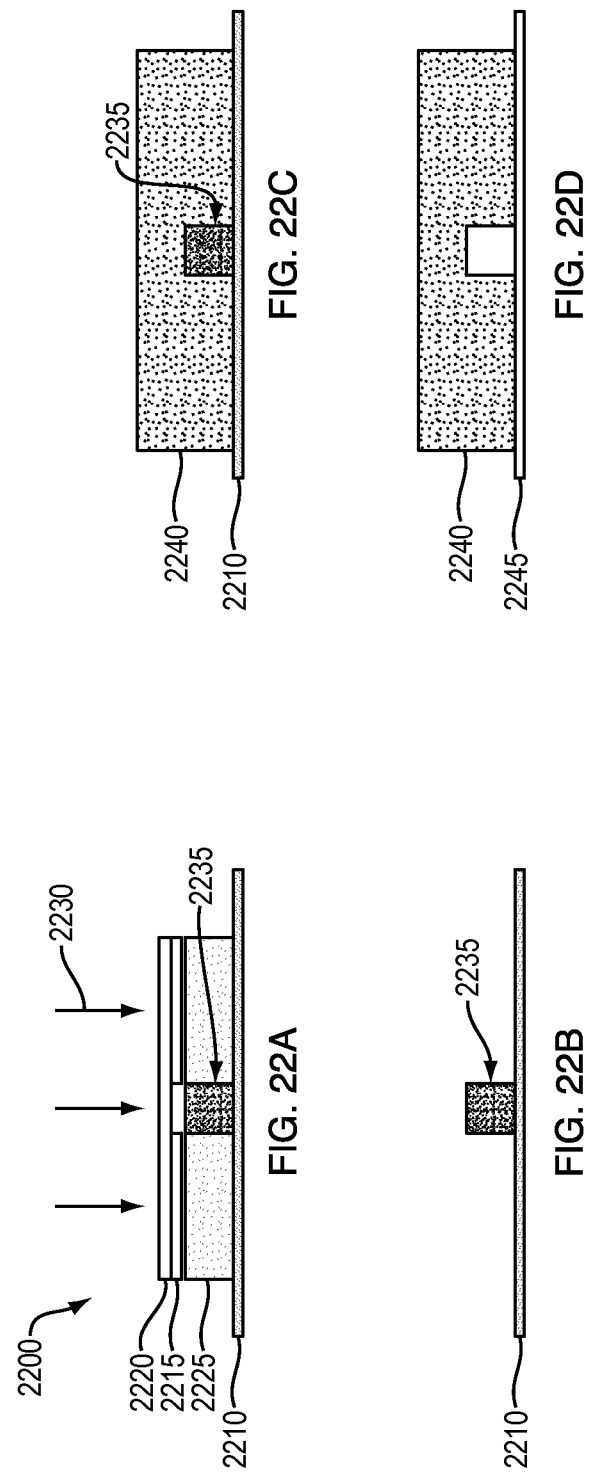

MICROFLUIDIC ASSAY FOR RAPID OPTIMIZATION OF CELL ELECTROPORATION

RELATED APPLICATION

This application is the U.S. National Stage of International Application No. PCT/US2014/069615, filed on Dec. 10, 2014, which designates the U.S., published in English, and this application claims the benefit of U.S. Provisional Application No. 62/020,959, filed on Jul. 3, 2014. The entire teachings of the above applications are incorporated herein by reference.

GOVERNMENT SUPPORT

This invention was made with Government support under Grant No. 6928282 awarded by DARPA. The Government has certain rights in this invention.

BACKGROUND OF THE INVENTION

Electroporation is an established microbiology and biotechnological tool that results from exposure of cells to external electric fields of sufficient strength to disrupt a plasma membrane of microorganisms and cells. Exposure of the microorganisms or cells to the external electric fields induces an increase in the local trans-membrane voltage (TMV). When the local TMV exceeds a critical threshold value, it is well-accepted that pores are created through the membrane of the cells, allowing for transport of ions and macromolecules across the membrane. Associated with the disruption of the cell membrane is an increase of permeability of the membrane to foreign molecules, including foreign nucleic acids or proteins, that may translocate through the pores and into the cells.

There is vast empirical evidence in the literature establishing trial-and-error protocols to increase electrocompetency of cells in a process that is time consuming and without real-time feedback. There are currently no protocols for measuring and improving the electrocompetency of cell structures without going through an empirical electroporation process. For example, determining the threshold value for electroporation typically involves a trial-and-error approach which can be time-consuming and inefficient. Therefore, there is a need for a rapid assay device that can be used to determine, for example, a threshold value for electroporation.

SUMMARY OF THE INVENTION

Flow-through electroporation methods have been developed by Geng et al. (Geng, T., et al., "Transfection of cells using flow-through electroporation based on constant voltage," *Nat. Protocols*, 2011. 6(8): p. 1192-1208.) for delivery of genes into cells and by Wang, et al. for electrical lysis of bacterial cells (Wang, H., A. Bhunia, and C. Lu, "A microfluidic flow-through device for high throughput electrical lysis of bacterial cells based on continuous dc voltage," *Biosensors and Bioelectronics*, 2006. 22(5): p. 582-588.).

Embodiments of the diagnostic assay disclosed herein differ from that of the group of Geng et al. (Geng, T. and C. Lu, "Microfluidic electroporation for cellular analysis and delivery," *Lab on a Chip*, 2013. 13(19): p. 3803-3821.) at least in that embodiments disclosed herein can be used to quantify rapidly electromagnetic field conditions required for inducing genetic transformation for cells whose transformation potential remains unexplored.

Embodiments disclosed herein provide for a rapid assay to visualize or detect and quantify electromagnetic field conditions required for successful electric field-assisted genetic transformation. An embodiment of the present application is an apparatus for cell electroporation comprising a structure. The structure encompasses a volume defining a cross-sectional area configured to contain cells having a plasma membrane and background media. The background media includes an exogenous agent capable of translocating across a plasma membrane in an electroporated state. An arrangement of electrodes may be arranged relative to the structure to produce levels of an electromagnetic field, at least one of the levels sufficient to electroporate at least a subset of the plasma membranes in at least a portion of the volume. The exogenous agent responsively translocates across at least some of the subset of plasma membranes in the electroporated state into cells to enable detection of cells having the exogenous agent therein, within the volume. The structure enables observation of a transition of cells without the exogenous agent therein to cells with the exogenous agent therein to enable correlating the transition to a threshold level of the electromagnetic field that causes cell electroporation.

An alternative embodiment of the present application is a method for performing cell electroporation comprising determining a threshold level of an electromagnetic field that causes electroporation of at least a subset of plasma membranes of cells within a portion of a volume of a structure. The volume of the structure defines a cross-sectional area with a capacity to accept an electromagnetic field having an electromagnetic field strength. The volume may include background media having an exogenous agent capable of translocating across a plasma membrane in an electroporated state induced at least in part as a function of the electromagnetic field strength. The determining includes observing, within the volume, a transition of cells without the exogenous agent therein to cells with the exogenous agent therein a parameter associated with the transition correlating to the threshold level.

An alternative embodiment of the present application is an apparatus for performing cell electroporation comprising means for encompassing a volume, the volume defining a cross-sectional area with a capacity to accept an electromagnetic field having an electromagnetic field strength. The volume includes cells having a plasma membrane and background media having an exogenous agent capable of translocating across a plasma membrane in an electroporated state induced at least in part as a function of the electromagnetic field strength. The apparatus further comprises means for applying the electromagnetic field to the volume to cause electroporation of at least a subset of the plasma membranes in at least a portion of the volume, and means for enabling observation in the volume of a transition of cells without the exogenous agent therein to cells with the exogenous agent therein. the location of the transition correlates to a threshold level of the electromagnetic field that causes cell electroporation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 22A-22D are representations of an example fabrication process of an embodiment of the device using soft lithography. (A) SU-8 lithography on Si wafer. (B) Washing away un-exposed SU-8. (C) Molding polydimethylsiloxane (PDMS) using SU-8 master. (D) Peeling PDMS off the SU-8 master and bond PDMS to a glass slide.

DETAILED DESCRIPTION OF THE INVENTION

A description of example embodiments of the invention follows.

The teachings of all patents, published applications and references cited herein are incorporated by reference in their entirety.

Embodiments of the present invention relate to an assay to determine parameters of an electromagnetic field that enable successful electroporation of plasma membranes.

Figure 1:
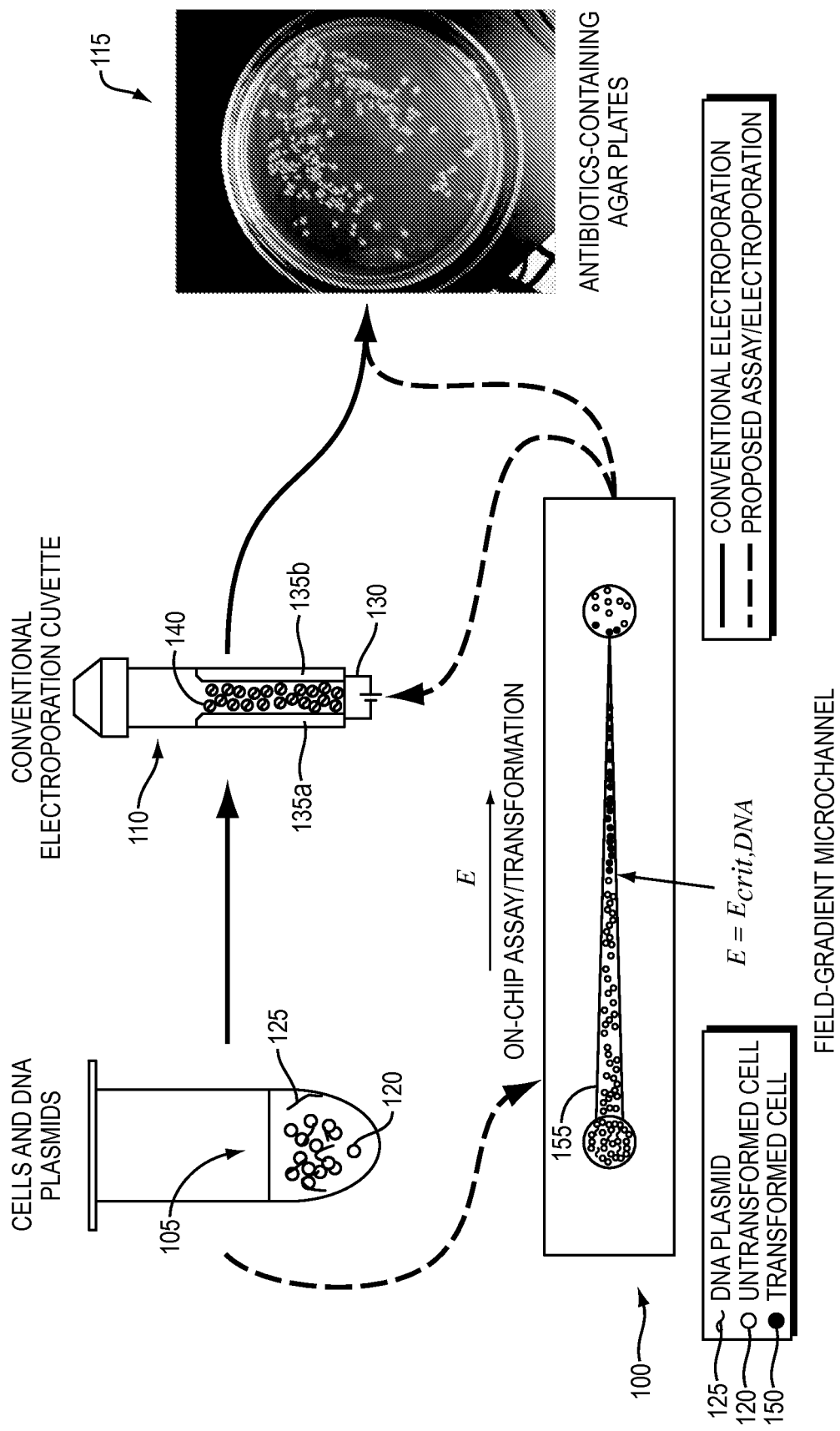
FIG. 1 is a schematic diagram of a genetic transformation assay in which the conventional (solid line arrows) and the presently disclosed (dashed line arrows) protocols for investigating bacterial transformation are shown. The presently disclosed protocol relates to a rapid assay that can be used to identify optimal electromagnetic field conditions for electroporation.

As shown in FIG. 1, conventional electroporation is conducted by a trial and error approach in which a solution 105 containing cells 120 and plasmid DNA 125 is placed into an electroporation cuvette 110. A voltage 130 is applied to electrodes 135a and 135b in contact with the electroporation cuvette 110 to generate an electric field, E. The electric field, E, may be a uniform electric field. Following electroporation, exposed cells 140, which may or may not have received the plasmid DNA 125, are transferred to agar plates 115 for colonization and to determine if electroporation was successful. The process for conventional electroporation is represented by a solid line in FIG. 1.

An embodiment of the present invention is an assay 100, containing a volume 155. The volume 155 may be a channel or a flowpath within which a solution of cells 120 and plasmid DNA 125 is placed. An electric field, E, is applied to the volume, such that the electric field magnitude varies within the volume 155 and such that a transition from untransformed cells 120 to transformed cells 150 is detectable and correlates to a critical value of E, $E_{crit}$. The general process for utilizing the assay is represented by a dashed line in FIG. 1.

In one embodiment, the device is used as a high-throughput device to screen for the threshold electromagnetic field for electroporation. In this high-throughput screening device, the duration of the electromagnetic field is determined by the duration of the voltage applied through the electrodes and the field strength depends on the local cross-sectional area. Cells at the same cross section experience approximately the same electromagnetic field, and establish a set of data for one statistical sample. Cells at different cross sections along the flow path experience different electromagnetic fields, and establish sets of data for different statistical samples. These sets of data from different statistical samples can be plotted and analyzed to determine the threshold electromagnetic field for electroporation.

The above described process embodiment provides identification and quantification of the electromagnetic field conditions required for the onset of electroporation. Once $E_{crit}$ is ascertained, electroporation utilizing a conventional electroporation cuvette may proceed. Alternatively, the electroporated cells from the assay may be directly cultured.

To induce electroporation, an electromagnetic field may be applied to the volume, consisting of an electric field and/or a magnetic field. In an alternative embodiment an optical field may be applied to induce electroporation. In a further alternative embodiment, the plasma membrane may be compromised to allow entry of exogenous material through heating. Thermal sources (e.g., Joule heating) applied to the volume may be utilized instead of, or in conjunction with, electrodes. The membrane's mechanical rigidity may also be changed, which may alter its permeability to exogenous species such as nucleic acids, by changing the osmolality of the solution.

An embodiment of the present application is an apparatus for cell electroporation comprising a structure. The structure encompasses a volume defining a cross-sectional area configured to contain cells having a plasma membrane and background media. The background media includes an exogenous agent capable of translocating across a plasma membrane in an electroporated state. An arrangement of electrodes may be arranged relative to the structure to produce levels of an electromagnetic field, at least one of the levels sufficient to electroporate at least a subset of the plasma membranes in at least a portion of the volume. The exogenous agent responsively translocates across at least some of the subset of plasma membranes in the electroporated state into cells to enable detection of cells having the exogenous agent therein, within the volume. The structure enables observation of a transition of cells without the exogenous agent therein to cells with the exogenous agent therein to enable correlating the transition to a threshold level of the electromagnetic field that causes cell electroporation.

Alternative embodiments of the present invention further comprise an electrical power source coupled to the arrangement of electrodes, the power source configured to stimulate the electrodes to produce the electromagnetic field, the exogenous agent responsively translocating across at least a subset of the plasma membranes in the electroporated state into cells. The electrical power source may be an AC signal generator, a DC power supply connected to a high frequency switch/relay, a multiple-output DC power supply, or an arbitrary function generator coupled to a high-voltage amplifier.

Embodiments of the present invention may include multiple arrangements of electrodes arranged in electromagnetic proximity to the volume. The arrangement of electrodes may include at least one reference electrode and multiple signal electrodes, at least one signal electrode and multiple reference electrodes, at least one pair of electrodes positioned at opposing ends of the volume, at least one pair of electrodes positioned laterally across the volume along at least a portion of a length of the volume, at least one pair of electrodes positioned circumferentially in a perpendicular direction to a length of the volume, at least one pair of electrodes positioned in a helical configuration along a length of the volume, at least one pair of electrodes positioned axially along a length of the volume, at least one pair of electrodes positioned in a coaxial configuration along a length of the volume. At least one pair of electrodes may be isolated from the volume via a solid, fluid, or gas barrier. The electrodes may be metallic in nature, highly electrically-conductive solutions, or any combination thereof.

Embodiments of the present invention may contain a static solution of the plasma membranes and the background media. In an alternative embodiment, the volume may be a flow path or channel. The volume may contain a static solution of the cells and the flowpath may deliver a background buffer having the exogenous agent therein. The static solution of the cells and the background buffer may be achieved by using hydrogels within the entirety of the 3D volume by cross-linking polymerization with ionic, light-induced and/or thermal methodologies. The static solution of the cells may be achieved by coating the apparatus with chemicals or immobilizing the cells in hydrogels within the entirety of the volume by cross-linking polymerization with ionic, light-induced and/or thermal methodologies. The volume may be in fluid association with an inlet port and an outlet port that permit a solution of the cells having a plasma membrane and the background media to flow into and out of the volume, respectively.

Embodiments of the present invention may include a cross-sectional area that varies across a dimension of the volume. The cross-sectional area may be tapered, tapered bidirectionally toward a center cross-sectional area, or tapered bidirectionally toward a region within the volume. The volume may define a cross-sectional area that decreases from an inlet reservoir to an outlet reservoir, the inlet reservoir and the outlet reservoir located on opposing ends of the volume; a cross-sectional area that decreases from an inlet reservoir to a length along the volume and then increases from the length along the volume to an outlet reservoir, the inlet reservoir and the outlet reservoir located on opposing ends of the volume; or, a cross-sectional area that constricts with a curved geometry. The curved geometry may result in a linear electromagnetic field gradient within the volume. The cross-sectional area geometry may be least one of the following: circular, triangular, square, rectangular, ellipsoidal, trapezoidal, pentagonal, hexagonal, octagonal, or star-shaped. Two arrangements of cross-sectional areas may be arranged in series, in parallel, or a combination thereof.

Embodiments of the present invention include cells having a plasma membrane that are eukaryotic cells, prokaryotic cells, mammalian cells, plant cells, bacterial cells, archael cells, yeast cells, or fungi cells.

Embodiments of the present invention may include an electromagnetic field that is an electrical field or an optical field. The electromagnetic field may be time dependent. The electromagnetic field may include at least one of the following waveforms: pulse waveforms, sinusoidal waveforms, frequency-modulated waveforms; sawtooth waveforms, exponentially decaying pulses, exponentially increasing pulses, triangular, trapezoidal, ramp up, ramp down, or square waveforms. The electromagnetic field may have a distribution within the volume that varies spatially within the volume. It may include a distribution that is exponential, linear, semi-linear, quadratic, or other mathematically-shaped function.

Embodiments of the present invention may include an exogenous agent that is a label or probe. Detecting cells having the exogenous agent therein may include observing the labeled exogenous agent in a visible wavelength band, an infrared wavelength band, or an ultraviolet wavelength band. Alternative embodiments may include detecting plasma membranes with the exogenous agent therein by electronically observing such membranes through an impedance measurement. Correlating the transition to a threshold level of the electromagnetic field may be a function of location of the transition within the structure, a function of timing of the transition within the structure, or a function of the magnitude of the electromagnetic field within the structure.

Embodiments of the present invention may include an exogenous agent that cannot penetrate the plasma membranes in an unelectroporated state and can be detected within the plasma membranes in an electroporated state, or the exogenous agent cannot penetrate the plasma membranes in an unelectroporated state and causes a physically or chemically observable change in the cells or plasma membranes in an electroporated state. The exogenous agent may be a label that can be detected after contact with intracellular substances. The exogenous agent may include at least one of the following: nucleic acid, amino acid, protein, drug, chemical, oligonucleotide, CRISPR sequence, polysaccharide, enzyme, therapeutic, vaccine, or plasmid DNA. The nucleic acid may be ribonucleic acid or deoxyribonucleic acid.

Embodiments of the present invention may include an electromagnetic field with a magnitude produced as a function of at least one of the following: temperature, electrical conductivity, pH, cell concentration, background buffer, osmolality, electric field pulse shape, electric field pulse duration, electric field gradient, or factors known to affect electroporation within the respective channel. The electromagnetic field may have a pulse duration selected of from about 10 ns to about 0.25 ms, from about 0.25 ms to about 5.0 ms, from about 0.01 ms to about 0.50 ms, from about 0.1 ms to about 2 ms, from about 1 ms to about 10 ms, from about 3 ms to about 50 ms, or from about 0.25 ms to about 50 ms. The electromagnetic field may have a magnitude between the range of 0.1 kV/cm and 100 kV/cm. The electromagnetic field may have a magnitude selected of from about 0.25 kV/cm to about 10 kV/cm, from about 1 kV/cm to about 20 kV/cm, from about 5 kV/cm to about 50 kV/cm, from about 7.5 kV/cm to about 15 kV/cm, from about 0.25 kV/cm to about 50 kV/cm; or from about 50 kV/cm to about 250 kV/cm.

Figure 2:
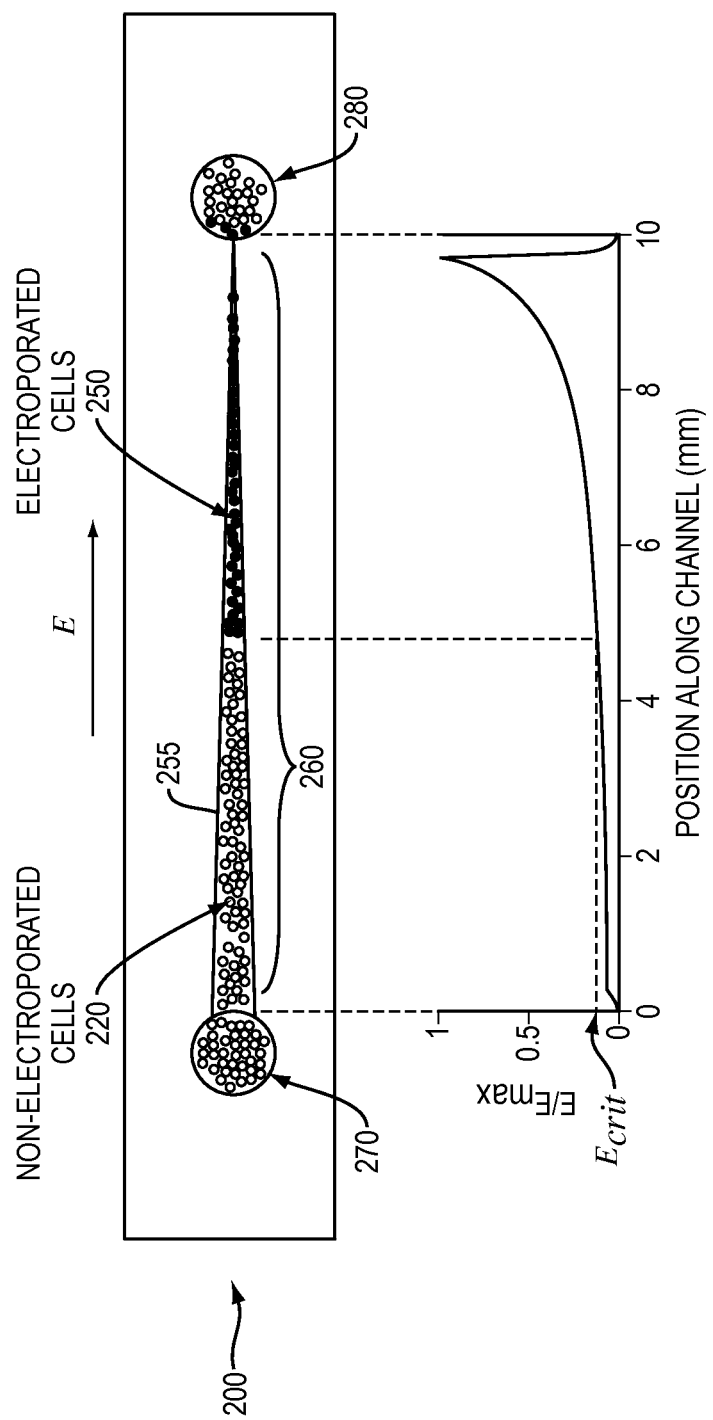
FIG. 2 is a schematic diagram (top view) of a rapid assay employing a converging microchannel to determine a minimum electric field required for electroporation of a given cell type bacterium. In this converging microchannel, the electric field magnitude varies with position along the channel (normalized by the maximum value). Electroporation occurs only in the regions where the local field exceeds a critical threshold for pore formation, which is denoted as "$E_{crit}$," for a specific set of electromagnetic pulse parameters and electrode configuration.

Turning to FIG. 2, an embodiment 200 of the assay 100 of FIG. 1 is depicted with a volume 255 configured to contain cells and a background media. The background media contains an exogenous agent, such as a fluorescent dye and/or plasmid DNA, which, under normal culturing conditions, would not translocate across the plasma membranes of the cells and may further contain an electroporation buffer to facilitate cell transformation. The exogenous agent may be a label that is detectable.

Beneath the schematic of embodiment 200 in FIG. 2 is a corresponding graph of electric field distribution within the volume 255. The magnitude of the electric field as a function of position along the volume 255 is known and, thus, enables correlation of the location of the transition to electroporated cells within the volume to a critical level of the electromagnetic field conditions. Additional details are presented below following a brief description of FIG. 3.

Figure 3:
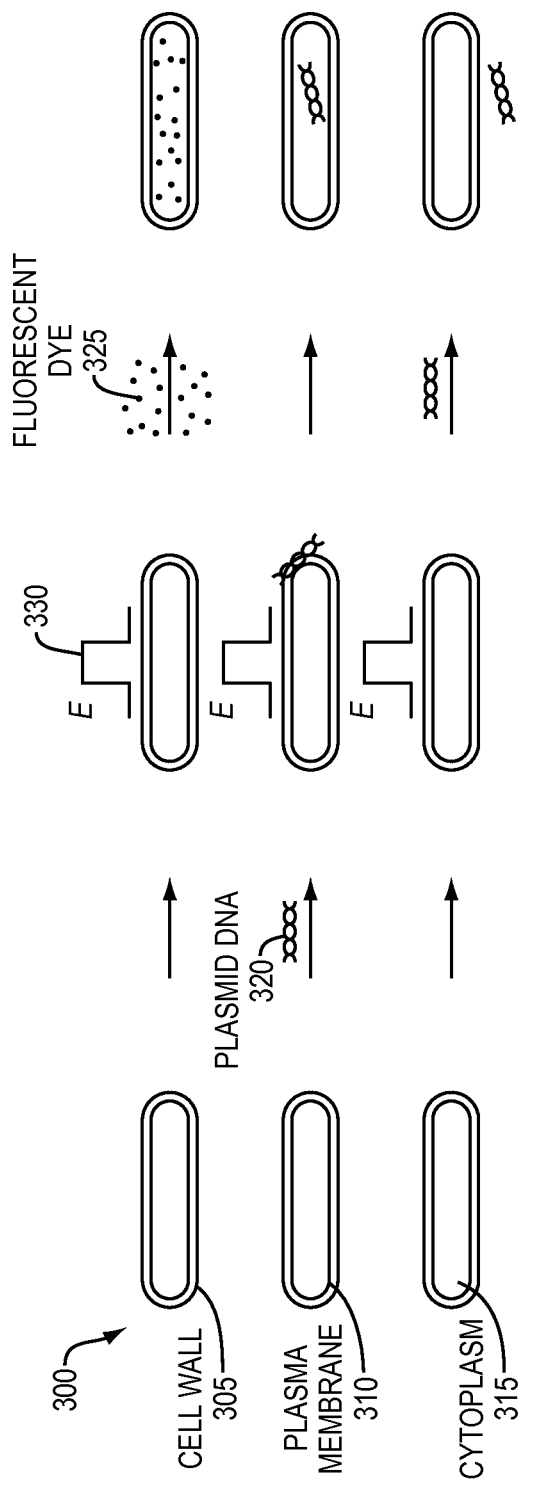
FIG. 3 is a representation of electroporation in a rod-shaped bacterium in the presence of a fluorescent dye and/or plasmid DNA before and after exposure to an external electromagnetic field.

A schematic representation of translocation during electroporation is shown in FIG. 3. Representative cells 300, shown as rod-shaped bacterium, include the structures of a cell wall 305, a plasma membrane 310, and cytoplasm 315. Application of the electrical pulse 330 results in an electrical field, E, which disrupts the plasma membrane 310 such that pores are created, permitting for the transport of ions and macromolecules across the membrane. This membrane disruption results in a non-linear increase in the electrical conductivity of the membrane that spans several orders of magnitude. Associated with the increase of the electrical conductivity of the membrane is the increase of membrane permeability to foreign molecules, including foreign proteins and nucleic acids, which may translocate through the pores and into the cell. In order for macromolecules, such as plasmid DNA 320, to successfully enter the cell, these molecules must be present before exposure to the external electric field, E. Timing is different for at least some smaller molecules, such as fluorescent dyes 325, which are still able to diffuse into the cells even after the application of the external electric field, E, but prior to the full recovery of the plasma membrane.

Returning to FIG. 2, the volume 255 in the embodiment shown has a constriction region 260 that varies in cross-sectional area across a dimension of the volume. In the embodiment shown, the constriction region 260 is a channel that tapers from a larger cross-sectional area to a smaller cross-sectional area between an inlet reservoir 270 and an outlet reservoir 280 located at opposing ends of the volume 255. An application of an electrical pulse to the volume results in an electrical field, E, of varying magnitude within the constriction region 260. In the embodiment shown, E increases in magnitude as the volume 255 tapers to smaller cross-sectional areas. At a threshold level of E, the onset of electroporation occurs. The location of electroporation of the cells resulting in uptake of the fluorescent dye and/or nucleic acid corresponds to the threshold level of E, labeled $E_{crit}$.

The cross-sectional area geometry may also be circular, triangular, square, rectangular, ellipsoidal, trapezoidal, pentagonal, hexagonal, octagonal, star-shaped, or any other arbitrary shape, or any combination of at least one of the above mentioned cross-sectional geometries.

The electric field distribution within the volume may be determined by solving a Laplace equation given by:

$$-\nabla \cdot (\sigma(|E|)\nabla \varphi) = 0 \quad (1)$$

where $\sigma(|E|, T)$ is the electrical conductivity of the electroporation buffer as a function of temperature (T) and electric field (E), and $\varphi$ is the electric potential. The electrical boundary condition at one electrode-volume interface may be set to the applied voltage $\varphi = V_{applied}$ (the voltage of the electroporation pulse), and the other electrode-volume interface to $\varphi = 0$. The remaining boundaries of the volume may be treated as electrically insulating, mathematically described by $d\varphi/dn = 0$, where n represents the axis perpendicular to the surface. More detailed procedures to calculate the electric field are described by Garcia et al. (Garcia, P. A., et al., "Intracranial Nonthermal Irreversible Electroporation: In Vivo Analysis," *J. Membr Biol*, 2010. 236(1): p. 127-136), the teachings of which are incorporated herein by reference. More detailed descriptions to calculate the fluid flow and temperatures due to Joule heating are described by Sano et al. (Sano, M. B., et al., "Joule heating effects on particle immobilization in insulator-based dielectrophoretic devices," Electrophoresis, 2014. 35(2-3):352-361), the teachings of which are incorporated herein by reference.

Figure 4A:
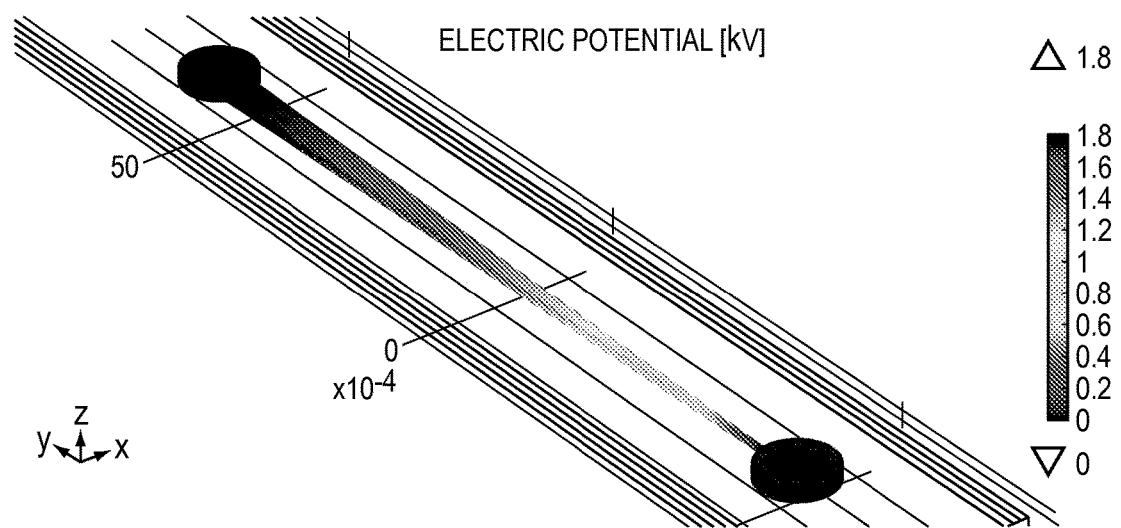
FIGS. 4A-4B are computational results of (A) electromagnetic (e.g., electric) potential and (B) electromagnetic field distributions to determine the $E_{crit}$ required for electroporation.
Figure 4B:
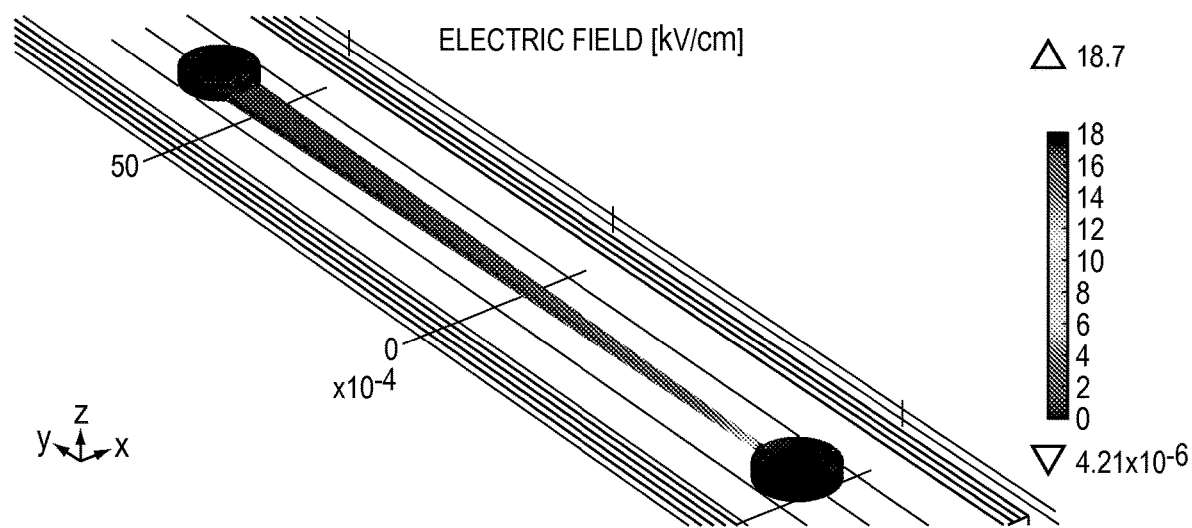
Figure 5A:
FIGS. 5A-5J are representations of bacteria undergoing electroporation over time in an embodiment of an apparatus described herein. The red dashed line indicates a transition from cells without an exogenous agent therein to cells with an exogenous agent therein.
Figure 5F:
Figure 5B:
Figure 5G:
Figure 5C:
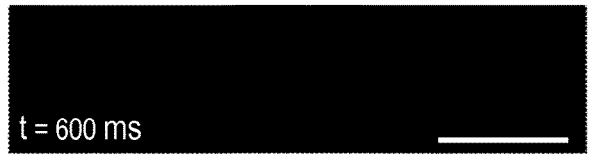
Figure 5H:
Figure 5D:
Figure 5I:
Figure 5E:
Figure 5J:

For the embodiment 200, the calculated electric potential and electric field distributions are shown in FIGS. 4A and 4B. The embodiment 200 employed a converging channel with a 20:1 constriction ratio between the inlet reservoir 270 and the outlet reservoir 280. The electric field generated has an exponential profile along the length of the channel.

For the embodiment 200, the results of electroporation of *E. coli* BL21 gram-negative bacteria are shown in FIG. 5. Florescence enhancement as a function of time is shown following the delivery of a 3000 V pulse with a duration of 5.0 ms. $E_{crit}$ may be determined as the magnitude of the electric field at the location at which fluorescence begins, represented by a dashed line.

Figure 6:
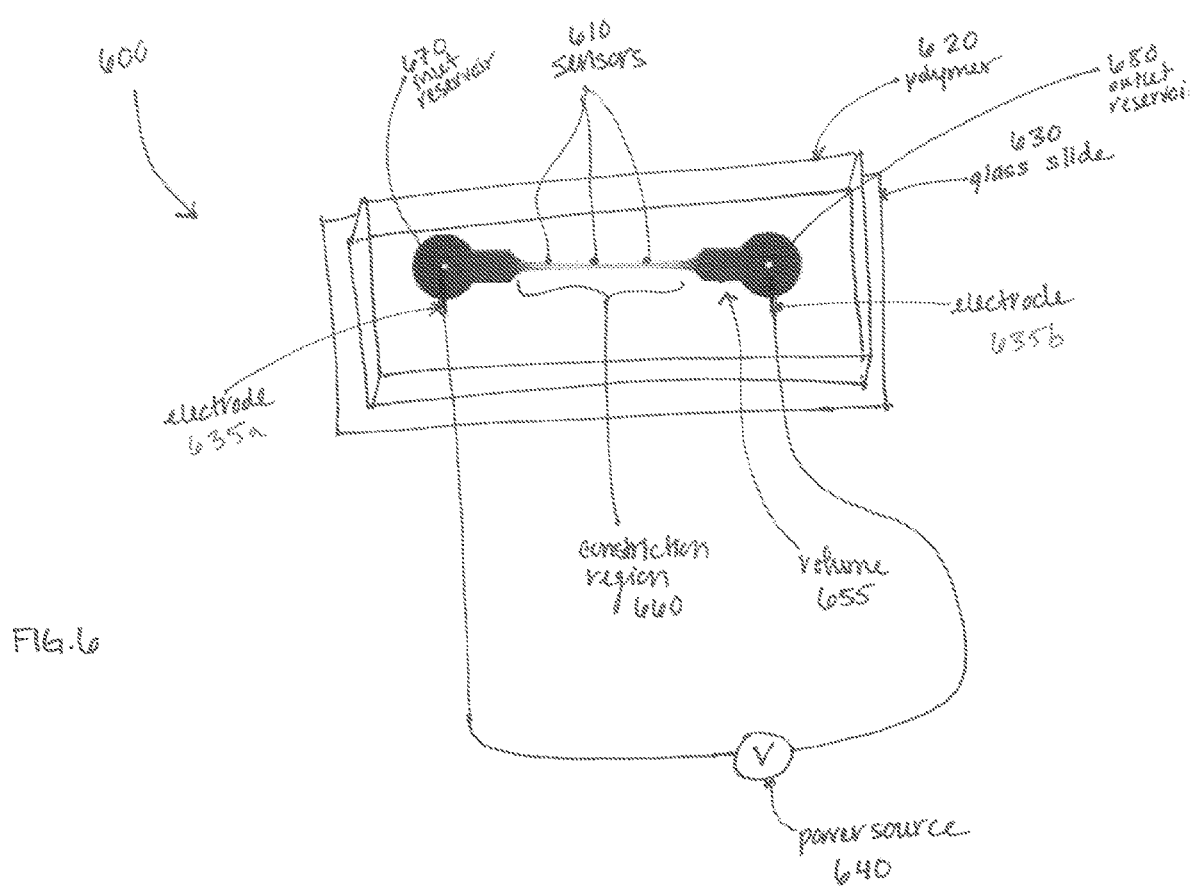
FIG. 6 is a mechanical schematic diagram of an embodiment of an apparatus described herein.
Figure 7A:
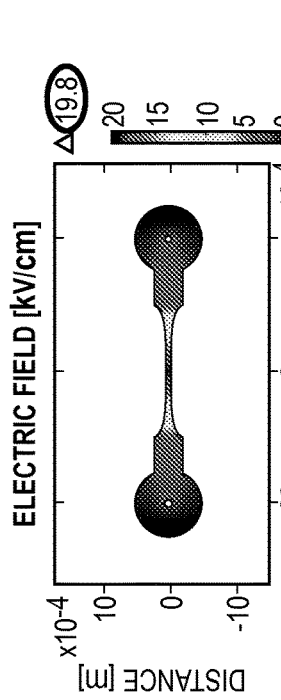
FIGS. 7A-7F are computational results of an electromagnetic (e.g., electric) field (A, C, E) and temperature (B, D, F) distributions after exposure to a 5.0 ms exponentially decaying electric pulse of 3000V in 10% glycerol (0.01 S/m).
Figure 7B:
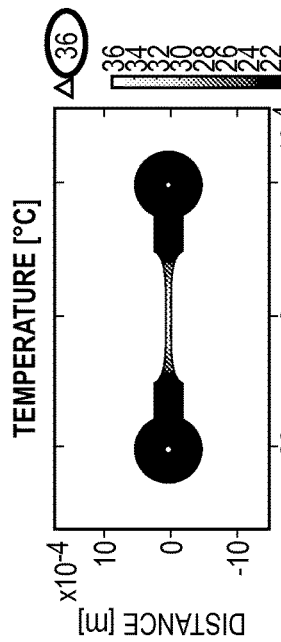
Figure 7C:
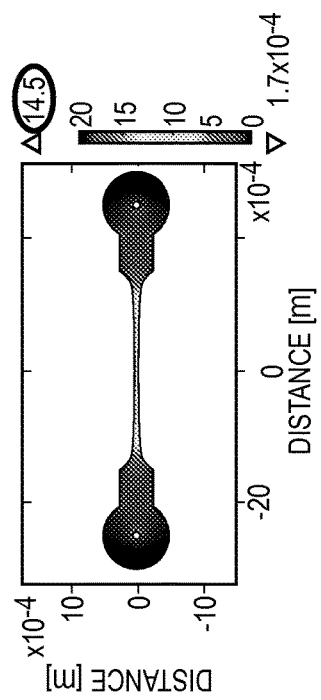
Figure 7D:
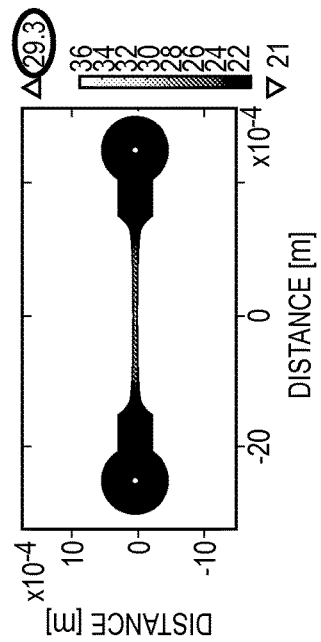
Figure 7E:
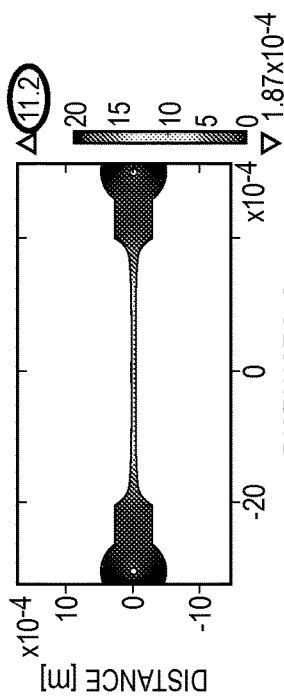
Figure 7F:
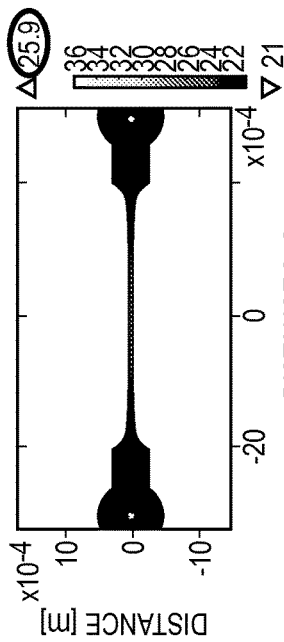

Turning to FIG. 6, application of the electric field pulse may be achieved by placing electrodes 635a, 635b relative to the structure 600 to produce an electromagnetic field within the volume 655. Electrodes 635a, 635b are shown positioned at opposing ends of the volume 655. Electrode 635a may be a signal electrode and electrode 635b may be a reference electrode. Alternative embodiments may have multiple arrangements of electrodes placed in proximity to the volume, such as at least one signal electrode and multiple reference electrodes, or one reference electrode and multiple signal electrodes. Additionally, electrodes may be placed laterally across the volume along at least a portion of the length of the volume. The electrodes 635a, 635b may be coupled to a power source 640, such as an AC signal generator, a DC power supply, a DC power supply connected to a high frequency switch/relay (not shown), or a multiple-output DC power supply.

The volume 655 contains a constriction region 660, within which electroporation occurs. This constriction region 660 may be a flowpath or a channel between an inlet reservoir 670 and an outlet reservoir 680, permitting a solution of plasma membranes and background media to flow through the volume 655. Alternatively, the volume 655 may contain a static solution of plasma membranes and background media. In the embodiment shown, the constriction region 660 has a cross-sectional area that tapers bidirectionally towards its center.

An alternative embodiment of the present invention is an assay 100, 600 containing a volume 155, 655. The volume 155, 655 may be a combination of a channel with immobilized cells (e.g., static) with a simultaneous flowpath (e.g., nutrients, dyes, DNA) that delivers the exogenous agents. This may allow for observation of the cells for extended period of time (e.g., minutes, hours, days) until the genetic transformation and/or replication processes are complete. The cells may be immobilized by coating the device with chemicals (e.g. Polydopamine) for cellular adhesion to the volume walls. Additionally, polymeric hydrogels may be used for encapsulating the cells within the entirety of the volume. The polymeric hydrogels can become active with ionic (e.g., Sodium Alginate with Calcium Chloride), light-induced (e.g., Photochemistry with UV or laser-induced), and/or thermal (e.g., UltraPure™ Agarose) cross-linking polymerization among other methodologies.

The ability to expose cells to a continuum of electric fields is important for optimization of electromagnetic conditions for successful gene transformation. Specifically, being able to detect the increase in fluorescence or expression of nucleic acid encoded proteins is a key strength of embodiments of the present application. By immobilizing the cells in a scaffold, such as a hydrogel, there is limited physical movement of the cells induced by the electric pulse or the fluid flow. Therefore, correlation of the electromagnetic conditions, such as an electric field magnitude, to the expression of the exogenous agents even after several seconds, minutes, hours, and/or days from the initial exposure is possible. In some embodiments, it may take hours/days for the cells to replicate and express the nucleic acid (i.e., it may take hours/days for cells to visually indicate successful gene transfer) so it is imperative to maintain the cells viable and allow for replication to occur. The simultaneous flow path regards the background buffer (e.g., electroporation buffer and/or growth media) that can penetrate through the hydrogel pores and deliver the nucleic acid during electroporation and/or nutrients to make maintain the cells viable until the expression of the specific dye, nuclei acid, and/or protein.

Returning to FIG. 6, the volume 655 of the structure 600 may be created within a polymer 620 or silicone substrate, such as polydimethylsiloxane (PDMS), placed on a glass slide 630. Alternatively the volume 655 could be machined out of glass or any other suitable low conductivity material. The volume may be viewable through the top or bottom of the structure 600, enabling observation of, for example, cells having the exogenous agent (e.g., label) therein to cells without the exogenous agent therein. The transition may be detectable through observation in a visible wavelength band, an infrared wavelength band, or an ultraviolet wavelength band. The transition may be observed by sensors 610 (in an electromagnetic region (e.g. visible wavelength, ultraviolet (UV) wavelength, infrared wavelength) of the electromagnetic spectrum) placed at locations within or adjacent to the volume, or it may be observable by a human eye, fluorescent microscope (e.g., confocal, inverted) and/or camera (not shown). Alternatively, the sensors 610 may detect the transition through electronic observation, such as through an impedance measurement.

It should be understood that a processor (not shown) separately coupled to the sensors 610 to determine a position of the transition may perform a correlation by way of, for example, a look up in a look-up table or a calculation, and may correlate the position of the transition to the threshold electromagnetic field level that caused the electroporation.

The constriction region 660, or channel, of the volume 655 may be manufactured to arbitrary lengths. The calculated electric field distributions and temperature distributions of embodiment 600 with varying channel lengths are shown in FIGS. 7A-7F. These embodiments demonstrate an effect that geometry may have on the resulting electric field gradients within the volumes. Specifically, the length and width of the channels were modeled to have 2.0-mm (FIGS. 7A, 7B), 3.0-mm (FIGS. 7C, 7D), and 4.0-mm (FIGS. 7E, 7F) active constrictions. The electric field distribution extending from the channel center along the centerline of these embodiments may be seen in FIG. 8, demonstrating that the constriction region reaches levels required for electroporation. The temperature increase after a 5.0-ms pulse with an exponentially decaying electric field was computed. The results confirm that there is an increase in temperature due to Joule heating, but, in a 10% glycerol buffer (as modeled), this increase is not sufficient to induce bacterial inactivation (killing) of most organisms as it reaches a maximum of 37.2° C. in the 2.0-mm device, which is the culture temperature for the bacteria. It should be understood that the maximum temperature reached is a function of the initial temperature, and the temperature that leads to cell or microorganism death depends upon the cell of interest.

Figures 9A, 9B, 9C:
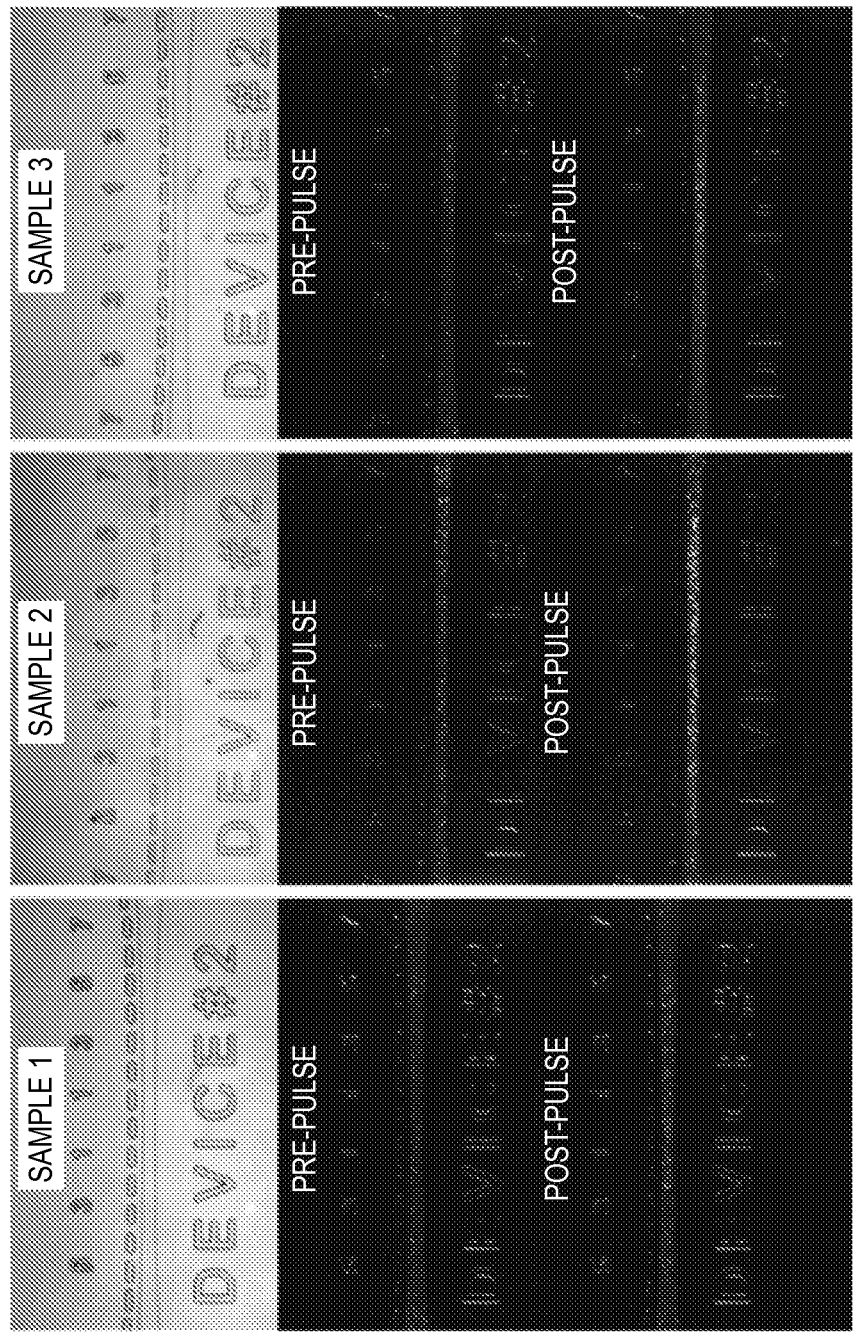
FIGS. 9A-9C are representations of bacteria undergoing electroporation over time in an embodiment of the device.

For the embodiment 600, the results of electroporation of *E. Coli* K12 gram-negative bacteria are shown in FIGS. 9A-9C. Images displaying fluorescent enhancement are shown pre- and post-pulse. Specifically, SYTOX® Green Nucleic Acid Stain (Life Technologies, Grand Island, N.Y.) was used as the exogenous agent, which, under normal conditions, is impermeable to the plasma membrane, but enters the plasma membrane when sufficiently high electric fields lead to pore formation. Electroporation occurred only in the regions where the local field exceeded the threshold for pore formation. A 3000 V exponentially decaying pulse was delivered with a time constant of 5.0 ms.

Figure 8:
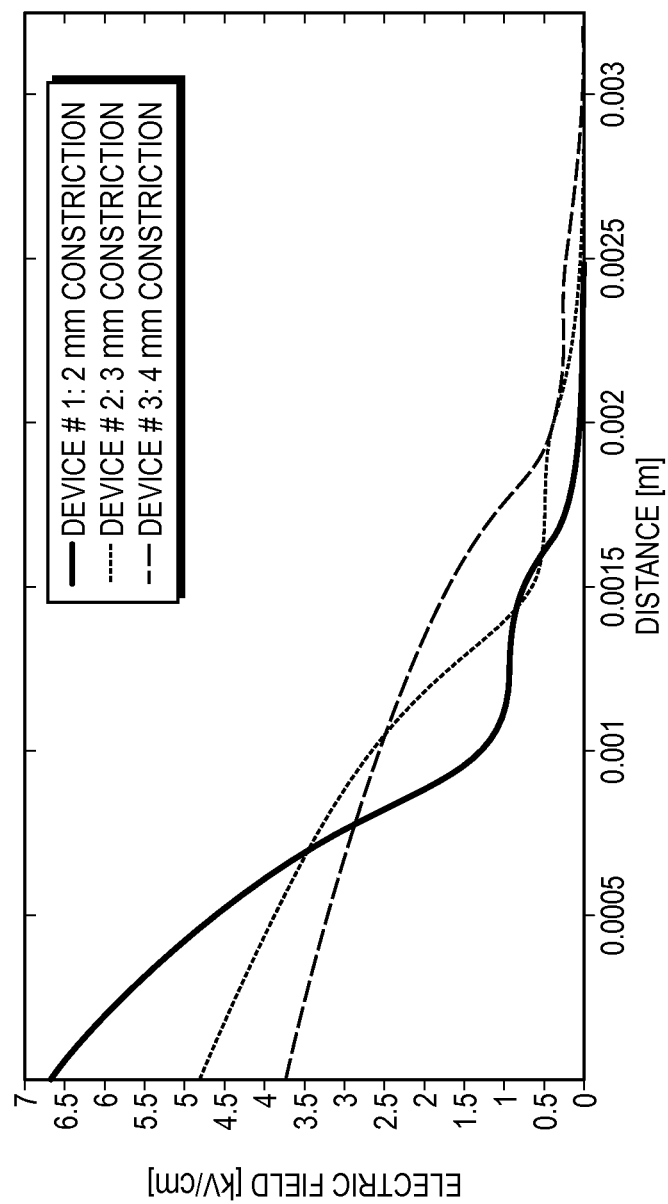
FIG. 8 is a graph displaying an electromagnetic (e.g., electric) field as a function of distance along the channel centerline for an embodiment of the device depicted in FIGS. 6 and 7.

As shown in FIG. 8, the gradient of the electric field distribution within the channel may vary over the length of the channel. The effects of such a distribution on electroporation can be seen in FIGS. 9A-9C for three different samples using identical electromagnetic conditions and device configuration.

Figure 10A:
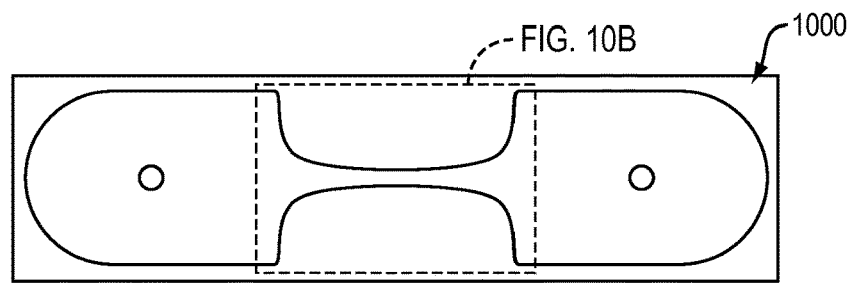
FIGS. 10A-10C are schematics of an embodiment of the device and corresponding graph of electric field vs. distance along the centerline of the device.
Figure 10B:
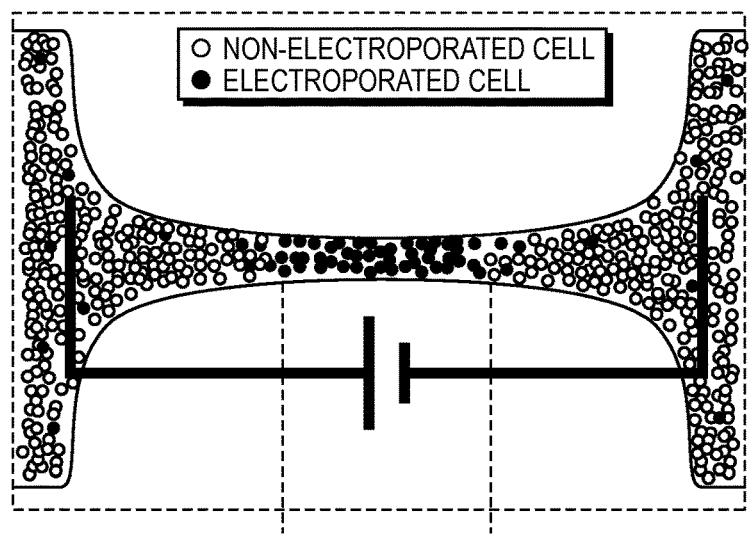
Figure 10C:
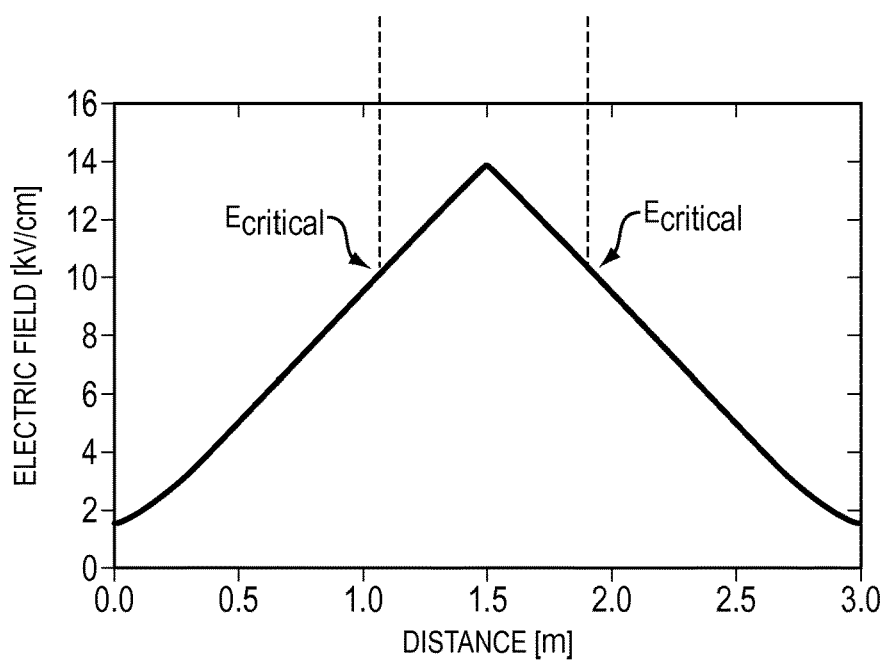

A geometry that results in a linear electric field gradient is shown in FIGS. 10A-10C, An embodiment 1000 contains a volume that has a cross-sectional area that constricts with a curved geometry. This curved geometry results in a linear electric field gradient, shown in FIG. 10C. The utility of this geometry is that a continuum of electric fields may be generated with one applied voltage. The simulated electric field curve of FIG. 10C was calculated with an applied voltage of 2.5 kV and was measured along the centerline of a channel within a 3.0-mm constriction region. The simulated electric field curve can be used to interrogate the threshold for successful electroporation. As shown in FIGS. 10B and 10C, the location of transition from non-electroporated cells to electroporated cells correlates to an ascertainable value of $E_{crit}$. Additionally, due to the symmetrical geometry of the embodiment 1000, two measurements of $E_{crit}$ are obtainable from a single experiment. For the embodiment 1000, the geometry of the constriction region may be tuned to have a steeper and sharper gradient of the electric field by modifying the constriction ratio from the outer regions of the volume to the constriction region.

Specifically in embodiment 1000 of the invention, a mathematically defined function was used to construct the constriction region geometry. The curve defining the volumes is given by:

$$w_2 = \frac{w_1}{1 + kx} \quad (2)$$

where $w_1$ [mm] is half-maximum width and $w_2$ [mm] is the half-width as a function of distance x [mm] along the length of the constriction region. The parameter k [mm$^{-1}$] defines the degree of tapering between the maximum and minimum dimensions within the constriction region. An embodiment of the present application may have $w_2$=1 [mm], k=15 [mm$^{-1}$], and a total constriction region length of 3.0 mm, corresponded to an x=1.5 [mm]. The curve may then be reflected about the x=0 plane in addition to the y=0 plane in order to generate a symmetric volume, as shown in embodiment 1000. This specific combination of parameters results in a minimum restriction region width of 0.085 mm. Finally; the device was extruded by 100 µm in the z-direction to generate the 3D volume used during the numerical simulations and experiments. The device can be modified by selecting any combination of parameters above in order to increase or decrease the constriction region length and the amplification level of the electric field.

Figure 11:
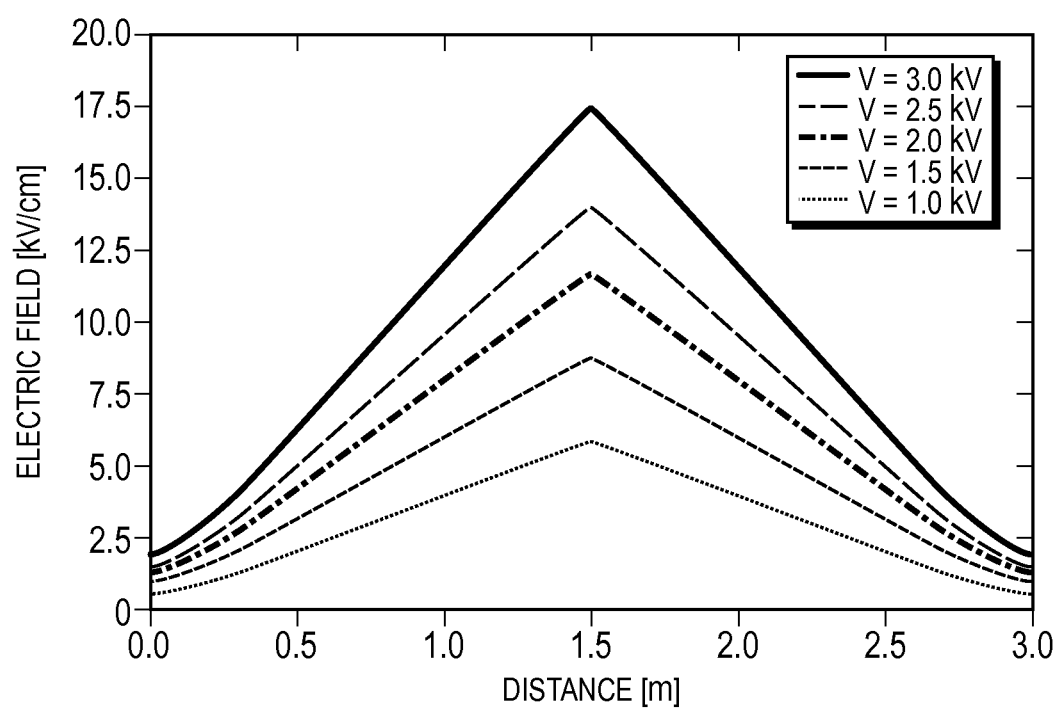
FIG. 11 is a graph of simulated electric fields for an embodiment of the device.

Simulated electric field curves for different applied voltages (1 kV-3 kV) are shown in FIG. 11 and demonstrate the linear gradient along the centerline of the microfluidic channel of embodiment 1000. The electric field ranges can be used to interrogate the threshold for successful electroporation using otherwise membrane impermeable fluorescent dyes to label cells and/or nucleic acid for successful transformation. Additionally, the assay may be used to determine the lethal electromagnetic conditions to achieve cell death in the device. Therefore, it is possible to assay a continuous spectrum of electric fields with only one experiment to determine the onset and extent of electroporation for a given set of conditions and the upper limit of electromagnetic conditions that result in cell kill.

Alternative embodiments of the present invention may include electromagnetic fields of other distributions within the volume, such as exponential increase, exponential decrease, semi-linear, quadratic, or other mathematically-defined function. Additionally, the electromagnetic field may be time-dependent and may include various waveforms, such as pulse waveforms, sinusoidal waveforms, sawtooth waveforms, exponentially decaying pulses, exponentially increasing pulses, triangular waveforms, ramp up, ramp down, and square waveforms. The electromagnetic field may be an electrical field or an optical field.

Embodiments of the present invention may have electromagnetic fields of varying pulse durations, ranging from about 0.01 ms to about 50 ms, and varying magnitudes, ranging from about 0.25 kV/cm to about 50 kv/cm. The magnitude of the electromagnetic field produced may be a function of temperature, electrical conductivity, pH, cell concentration, background buffer, electric field pulse shape, electric field pulse duration, electric field gradient, osmolality, and other factors known to affect electroporation.

FIG. 11 provides an example set of graphs that may be used to correlate distance from a midpoint between reservoirs of the embodiment 1000 of FIG. 10 with a corresponding electric field for which electroporation occurs to determine the threshold value for electroporation.

Figure 12A:
FIGS. 12A-12D are florescence micrographs (A, B) of *Corynebacterium glutamicum* undergoing electroporation in an embodiment of the device with corresponding graphs of intensity (C) and cumulative intensity (D).
Figure 12B:

For the embodiment 1000 of FIG. 10, the results of electroporation of *C. glutamicum* are shown in FIGS. 12A and 12B utilizing 5 µM of SYTOX® Green Nucleic Acid Stain (Life Technologies, Grand Island, N.Y.). Fluorescence micrographs are shown before (FIG. 12A) and after (FIG. 12B) delivery of a 1.8 kV exponentially decaying electroporation pulse of 1.0 ms duration in 0.01×PBS suspending buffer.

Figure 12C:
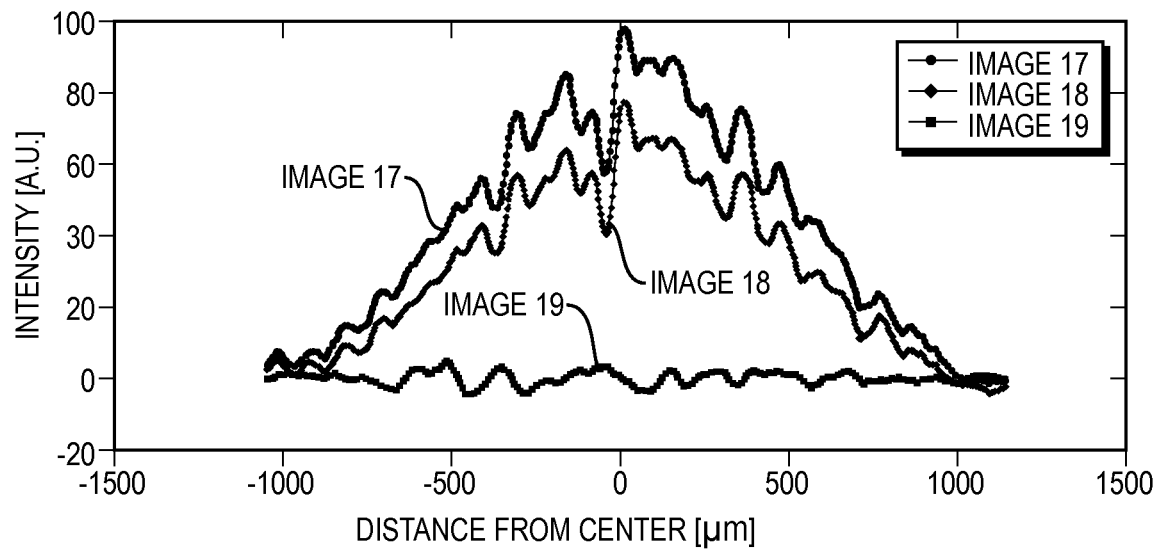

Plots of fluorescence intensity in arbitrary units (A.U.) versus position corresponding to the fluorescence images are shown in FIG. 12C and show a clear increase in cell fluorescence after the pulse. Image 17 (bottom, red curve) is the last image captured before the pulse; image 18 (middle, black curve) is captured during the pulse; and image 19 (top, blue curve) is captured after the pulse.

To attenuate noise, the intensity data may be averaged over the vertical extent of the channel and over 8 pixels in each direction along the channel. Additionally, a Gaussian filter may be applied to smooth the data further.

Figure 12D:
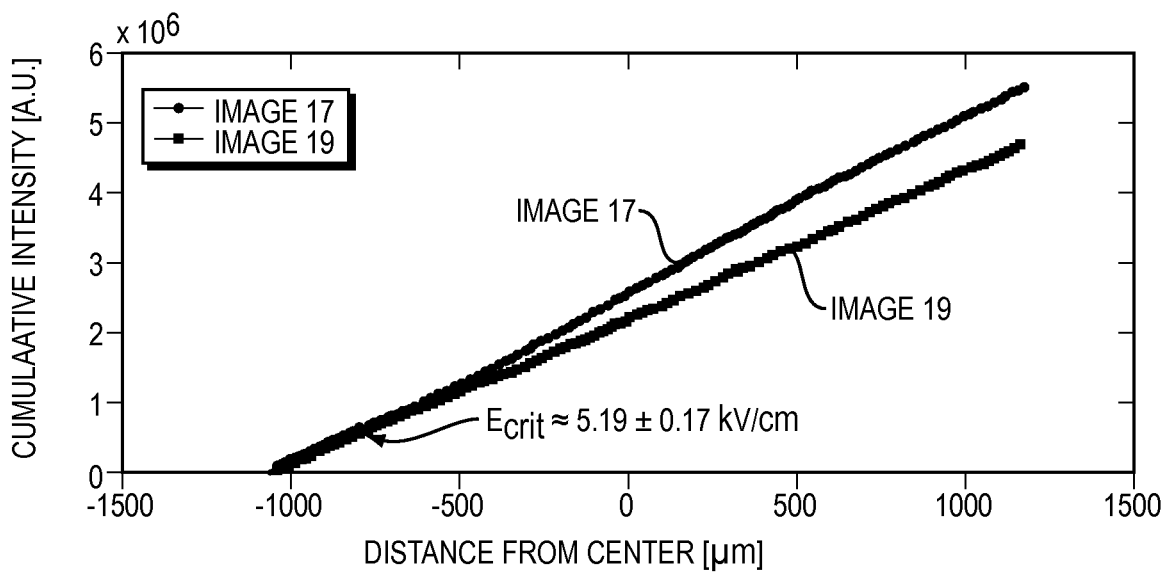

FIG. 12D displays cumulative fluorescence intensity versus position along a constriction region. The change in slope indicates the point at which electroporation begins. From this plot, and the associated simulation data, the critical electric field strength for electroporation, $E_{crit}$, may be extracted. For this particular experiment, the critical field was determined to be approximately 5.19±0.17 kV/cm, and the average critical field was 5.70±0.54 kV/cm (calculated over six trials conducted).

In the trials conducted and represented in FIGS. 12A-12D, the precise location of the onset of electroporation was visible to the naked eye. However, determining the precise location of the onset of electroporation may not always be apparent to the naked eye. For this reason, to determine $E_{crit}$ the data may be plotted cumulatively, as shown in FIG. 12D. The y-axis variable in this case is the cumulative intensity (CI), defined as $$CI(x_n) = \sum_{i=1}^{n} \left[ \sum_{j} I(x_i, y_j) \right] \quad (3)$$

where I is the fluorescence intensity (in arbitrary units) for a particular pixel, the index i corresponds to the horizontal direction along the channel (the leftmost pixel corresponds to i=1), and the index j ranges vertically between the red lines in FIGS. 12A and 12B. CI ($x_n$) is the summed fluorescent intensity from the left edge of the channel to the point $x_n$, over the pixels bounded by the two lines. At the channel location where electroporation begins, the overall fluorescence intensity increases and therefore the slope of the cumulative post-pulse (top, blue) curve in FIG. 12D increases. This location may be pinpointed as the point at which the electric field reaches its critical value to induce electroporation mediated introduction of exogenous agents. This transition location within the channel may then be correlated to the simulated electric field distribution, and the critical field intensity, $E_{crit}$, for electroporation may thereby be extracted.

Alternative embodiments of the present invention may enable correlation of the transition of non-electroporated cells to electroporated cells to $E_{crit}$ as a function of timing or as a function of the electromagnetic field conditions within the structure, such as magnitude, duration, pulse shape, pulse number and other features.

Figure 13A:
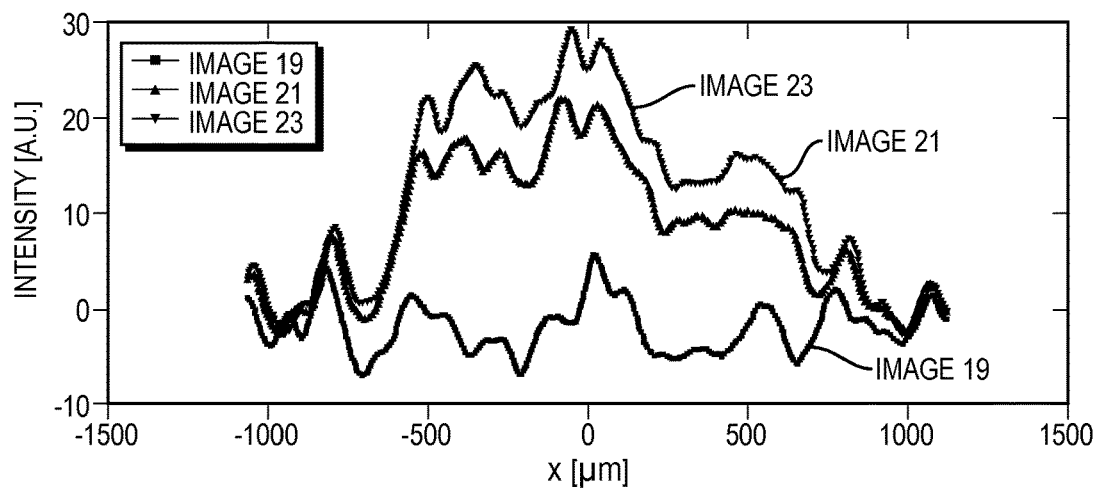
FIGS. 13A-13C are graphs of intensity (A), cumulative intensity (B), and intensity with background subtracted (C) of *Geobacter sulfurreducens* undergoing electroporation in an embodiment of the device.
Figure 13B:
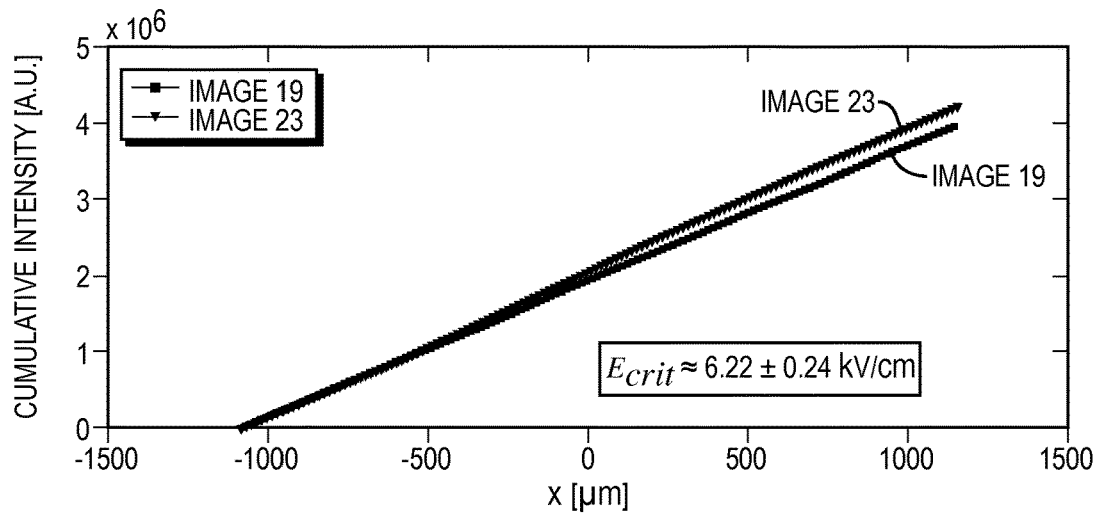
Figure 13C:
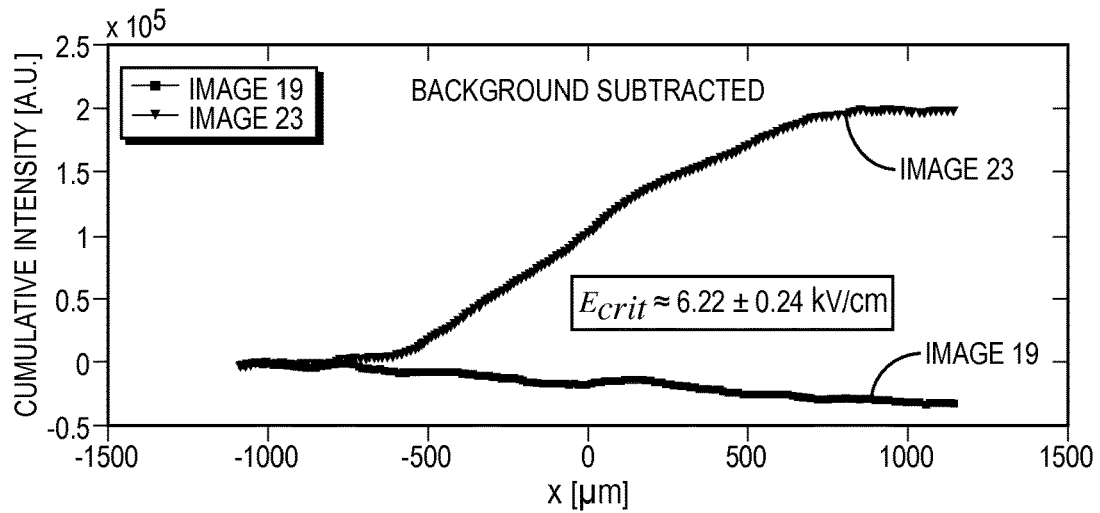

For the embodiment 1000, the results of electroporation of *Geobacter sulfurreducens* are shown in FIGS. 13A-13C. Fluorescent dye (SYTOX® (5 µM)) and a surfactant (Tween 20 (0.05% v/v)) mixture were prepared for the electroporation assay with one 2.1-kV exponentially decaying electroporation pulse (1.0 ms duration).

FIG. 13A shows plots of fluorescence intensity versus position corresponding to the fluorescence images, showing a clear increase in cell (*G. sulfurreducens*) fluorescence after the pulse. Image 19 (bottom, red curve) is the last image captured before the pulse; images 21 (middle, blue curve) and 23 (top, green curve) were captured after the pulse. To attenuate noise, the intensity data may be averaged over the vertical extent of the channel and over 8 pixels in each direction along the channel; additionally, a Gaussian filter may be applied to smoothen the data further.

FIG. 13B shows cumulative intensity versus position along the channel. The change in slope indicates the point at which electroporation begins. From this plot, and the associated simulation data, the critical electric field strength for electroporation, $E_{crit}$, may be extracted.

FIG. 13C shows cumulative intensity with background fluorescence subtracted and allows for easier identification of the transition between electroporated and non-electroporated cells. For this particular experiment, the critical field is approximately 6.22±0.24 kV/cm; over the six trials conducted, the average critical field was 6.35±0.24 kV/cm.

Figure 14A:
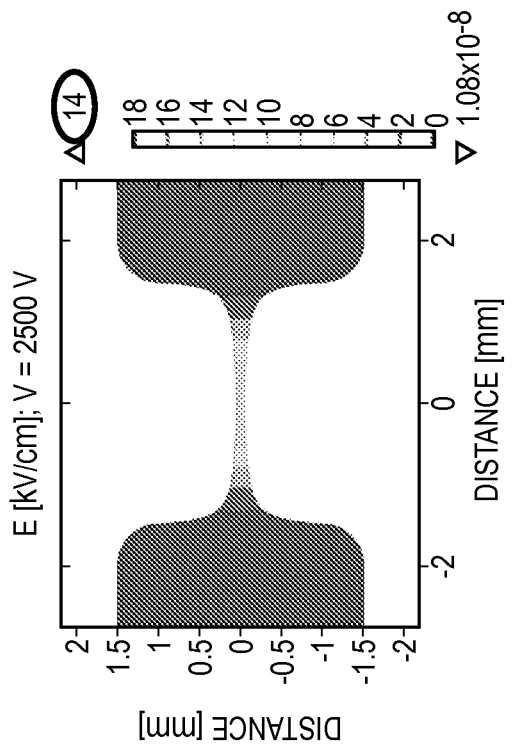
FIGS. 14A-14C are computational results of electric field distributions within an embodiment of the device for exponentially decaying pulses with applied voltages of (A) 2000 V, (B) 2500 V, and (C) 3000 V.
Figure 14B:
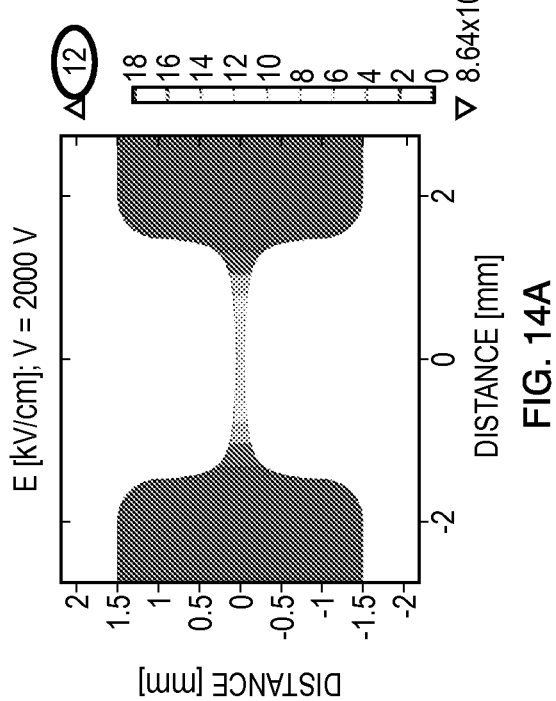
Figure 14C:
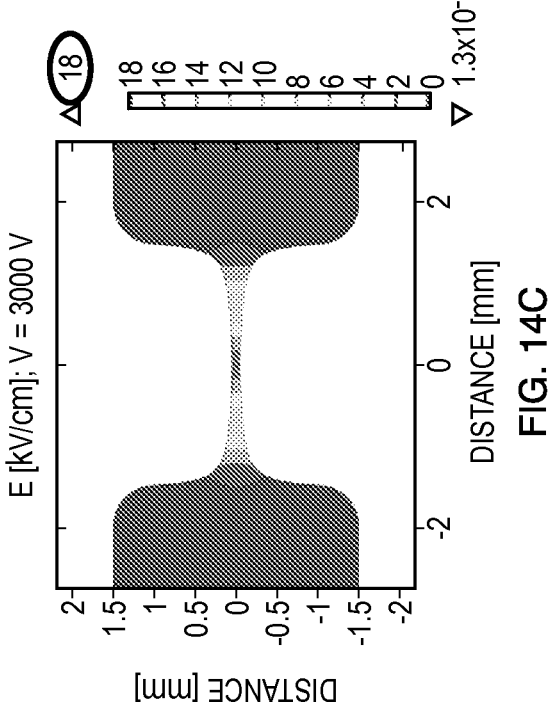

For embodiment 1000, FIGS. 14A-14C show the electric field distributions for exponentially decaying pulses with applied voltages of 2000 V (FIG. 14A), 2500 V (FIG. 14B), and 3000 V (FIG. 14C) and demonstrate sufficiently high electric fields to achieve electroporation of microorganisms. The maximum electric fields for each simulation are denoted within ellipses at the upper corner of each figure panel.

Figure 15A:
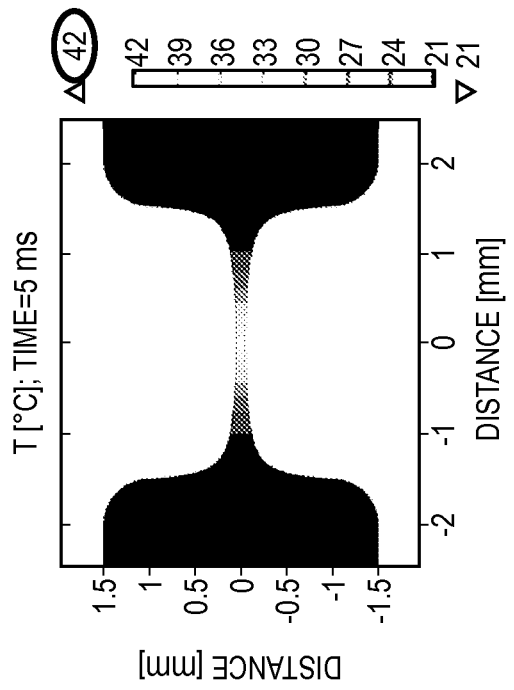
FIGS. 15A-15D are computational results of temperature distributions during and after the completion of a 5 ms exponentially decaying pulse of 2500 V in an embodiment of the device.
Figure 15B:
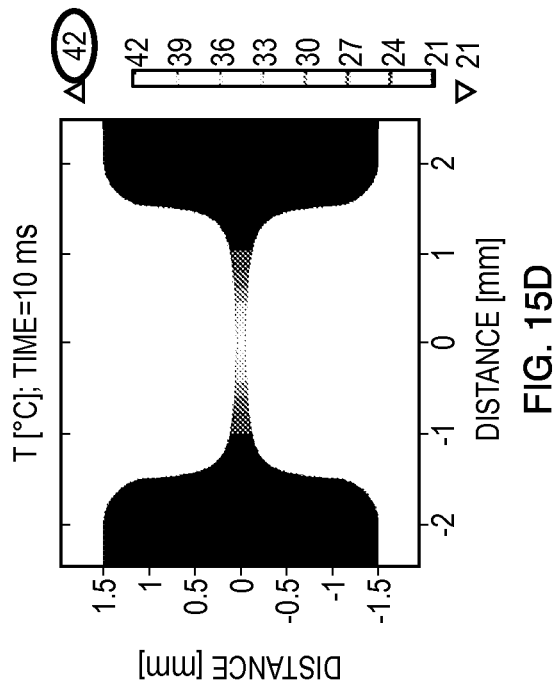
Figure 15C:
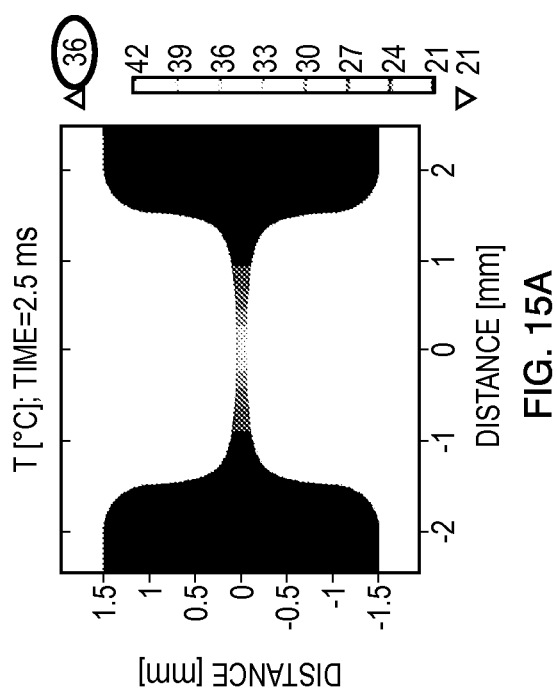
Figure 15D:
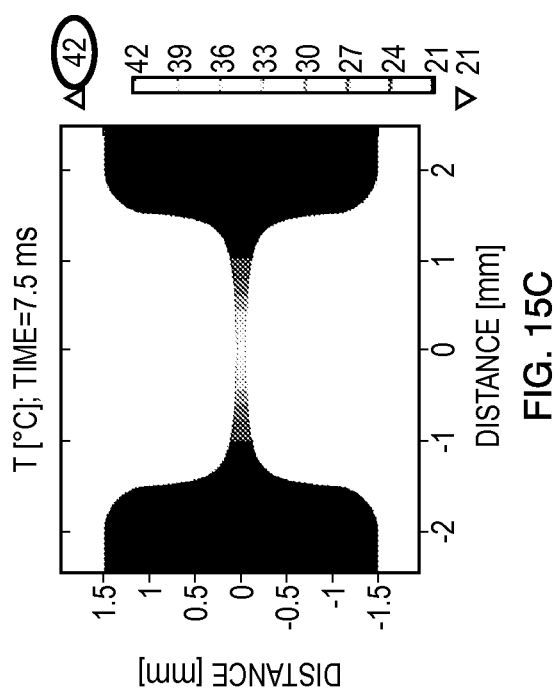

For embodiment 1000, FIGS. 15A-15D show temperature distributions during and after the completion of a 5 ms exponentially decaying pulse (2500 V) in 0.01×PBS (σ=0.02 S/m) at 2.5 ms (FIG. 15A), 5 ms (FIG. 15B), 7.5 ms (FIG. 15C), and 10 ms (FIG. 15D). The maximum temperatures for each simulation are denoted within ellipses at the upper corner of each figure panel.

Overall determination of the onset of electroporation was conducted for four different bacterial strains, including gram-positive, gram-negative, aerobic, and anaerobic bacteria. Genetic transformation of a fifth bacterial strain, *Vibrio cholera*, was also demonstrated using the present invention. The determination of the critical electrical fields for electroporation and DNA transformation is summarized in Table 1.

TABLE 1

Determination of critical fields for electroporation of various bacterial cells

| Organism | Device Generation | Voltage [kV] | Duration [ms] | $E_{crit}$ Assay [kV/cm] | On-chip Transformation |
|---|---|---|---|---|---|
| E. coli K12 | 2 | 3 | 5.9 | 8.43 ± 0.25 | |
| | 3 | 3 | 1.0 | 7.11 ± 0.63 | |
| E. coli BL21 | 3 | 2.5 | 1.0 | 6.89 ± 1.44 | Successful |
| C. glutamicum | 2 | 2.5 | 1.0 | 6.01 ± 0.26 | |
| | 3 | 1.8 | 1.0 | 5.70 ± 0.54 | |
| G. sulfurreducens | 3 | 2.1 | 1.0 | 6.35 ± 0.24 | |
| V. cholerae | 3* | 2.1* | 6.0* | Not Yet | Successful |

Embodiments of the present invention also apply to determining $E_{crit}$ for the plasma membranes of a variety of biological cells, including eukaryotic cells, prokaryotic cells, mammalian cells, plant cells, and bacterial cells.

In order to increase the throughput of the electroporated sample and increase the potential for transfection efficiency, a computational model to optimize experimental conditions may be utilized. The computational model numerically couples the fluid flow, electric, and thermal responses to determine the optimum flow rate that is required to expose cells to a subset of the continuous spectrum of the electric fields while allowing for heat dissipation generated by resistive heating. The results of simulations are shown in FIGS. 16-20 utilizing embodiment 1000 of the device with a channel depth of 100 µm that results in a sample volume of 0.084 µL within the constriction.

Initially, the residence time ($t_{res}$) of the cell sample volume of interest was estimated as a function of flow rate, Q. Additionally, the ratio of pulse duration ($\tau$) to residence time in the channel was computed to ensure that cells would be exposed to a subset of the continuous spectrum of the electric fields. An arbitrary parameter of $\tau/t_{res} \leq 5\%$ was used as an experimental condition that would be optimal for electroporation in order for the cells to be exposed to a narrow band of electric fields. The results are summarized in Table 2.

The shaded portion of Table 2 presents those flow rates and pulse durations that expose cells to a subset of the continuous spectrum of electric fields, but have relatively high residence (>100 ms) times. Conversely, the regions that are not shaded have much lower (<100 ms) residence times in the channel, which allows for completion of the electroporation procedure in a faster manner. However, using these parameters compromises the exposure to the desired subset of the continuous spectrum of electric fields since the cells travel along a larger portion of the constriction region for a given time. A flow rate of 50 µL/min (lightly shaded row) may be optimal for this particular device volume since the residence time is ~100 ms, which corresponds to the required ratio of $\tau/t_{res} \leq 5\%$ for all pulses between 1-5 ms while exposing cells to a subset of the continuous spectrum of the electric fields. The optimal flow rate may differ for channels with different volumes and lengths.

TABLE 2

Impact of flow rate on electric field exposure for pulse durations ($\tau$) of 1-5 ms

| Q [µL/min] | Q [µL/ms] | $t_{res}$ [ms] | $\tau = 1$ ms $\tau/t_{res}$ | $\tau = 2$ ms $\tau/t_{res}$ | $\tau = 3$ ms $\tau/t_{res}$ | $\tau = 4$ ms $\tau/t_{res}$ | $\tau = 5$ ms $\tau/t_{res}$ |
|---|---|---|---|---|---|---|---|
| 0 | 0.00E+00 | — | — | — | — | — | — |
| 5 | 8.33E-05 | 1010.64 | 0.10% | 0.20% | 0.30% | 0.40% | 0.49% |
| 10 | 1.67E-04 | 505.32 | 0.20% | 0.40% | 0.59% | 0.79% | 0.99% |
| 15 | 2.50E-04 | 336.88 | 0.30% | 0.59% | 0.89% | 1.19% | 1.48% |
| 20 | 3.33E-04 | 252.66 | 0.40% | 0.79% | 1.19% | 1.58% | 1.98% |
| 25 | 4.17E-04 | 202.13 | 0.49% | 0.99% | 1.48% | 1.98% | 2.47% |
| 30 | 5.00E-04 | 168.44 | 0.59% | 1.19% | 1.78% | 2.37% | 2.97% |
| 35 | 5.83E-04 | 144.38 | 0.69% | 1.39% | 2.08% | 2.77% | 3.46% |
| 40 | 6.67E-04 | 126.33 | 0.79% | 1.58% | 2.37% | 3.17% | 3.96% |
| 45 | 7.50E-04 | 112.29 | 0.89% | 1.78% | 2.67% | 3.56% | 4.45% |
| 50 | 8.33E-04 | 101.06 | 0.99% | 1.98% | 2.97% | 3.96% | 4.95% |
| 55 | 9.17E-04 | 91.88 | 1.09% | 2.18% | 3.27% | 4.35% | 5.44% |
| 60 | 1.00E-03 | 84.22 | 1.19% | 2.37% | 3.56% | 4.75% | 5.94% |
| 65 | 1.08E-03 | 77.74 | 1.29% | 2.57% | 3.86% | 5.15% | 6.43% |
| 70 | 1.17E-03 | 72.19 | 1.39% | 2.77% | 4.16% | 5.54% | 6.93% |
| 75 | 1.25E-03 | 67.38 | 1.48% | 2.97% | 4.45% | 5.94% | 7.42% |
| 80 | 1.33E-03 | 63.17 | 1.58% | 3.17% | 4.75% | 6.33% | 7.92% |
| 85 | 1.42E-03 | 59.45 | 1.68% | 3.36% | 5.05% | 6.73% | 8.41% |
| 90 | 1.50E-03 | 56.15 | 1.78% | 3.56% | 5.34% | 7.12% | 8.91% |
| 95 | 1.58E-03 | 53.19 | 1.88% | 3.76% | 5.64% | 7.52% | 9.40% |
| 100 | 1.67E-03 | 50.53 | 1.98% | 3.96% | 5.94% | 7.92% | 9.89% |

Figure 16B:
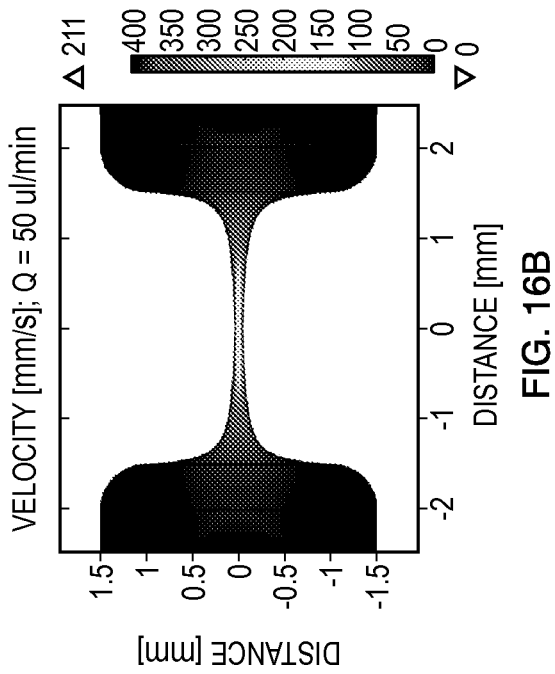
FIGS. 16A-16C are computational results of sample velocities for flow rates of (A) 25 μL/min, (B) 50 μL/min, and (C) 100 μL/min in an embodiment of the device.
Figure 16A:
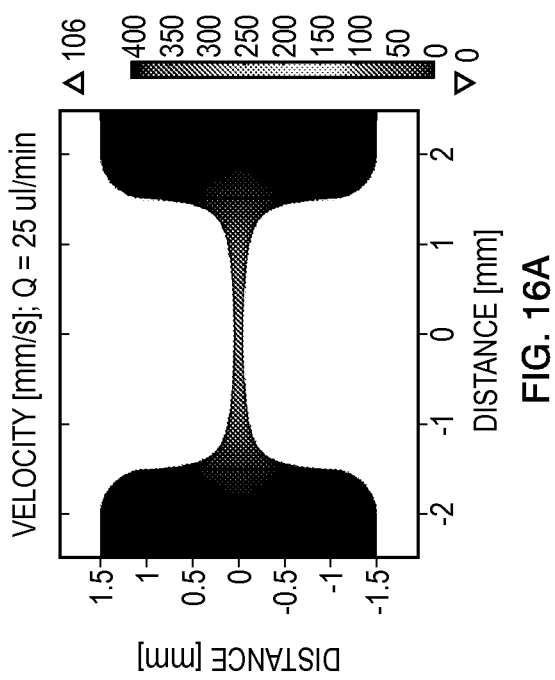
Figure 16C:
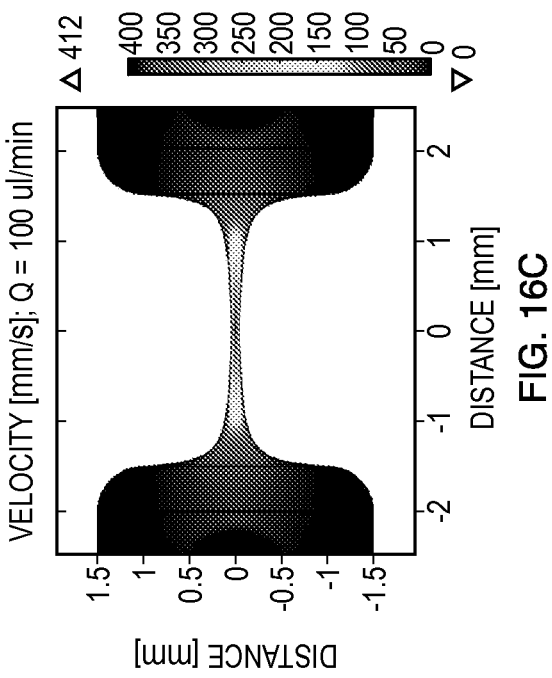
Figure 17A:
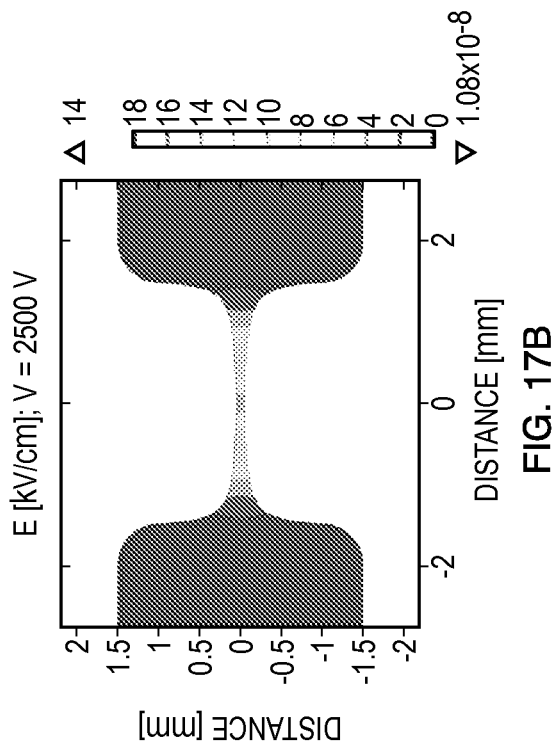
FIGS. 17A-17C are computational results of electric field distributions for applied voltages of (A) 2000 V, (B) 2500 V, and (C) 3000 V in an embodiment of the device.
Figure 17B:
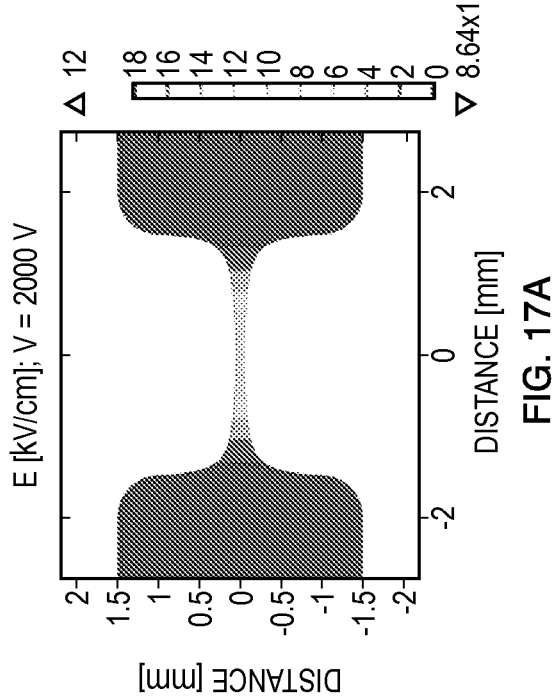
Figure 17C:
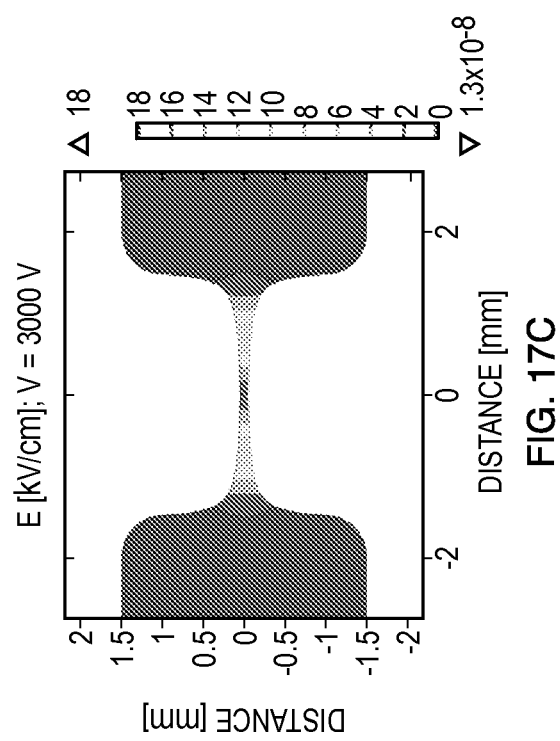
Figure 18A:
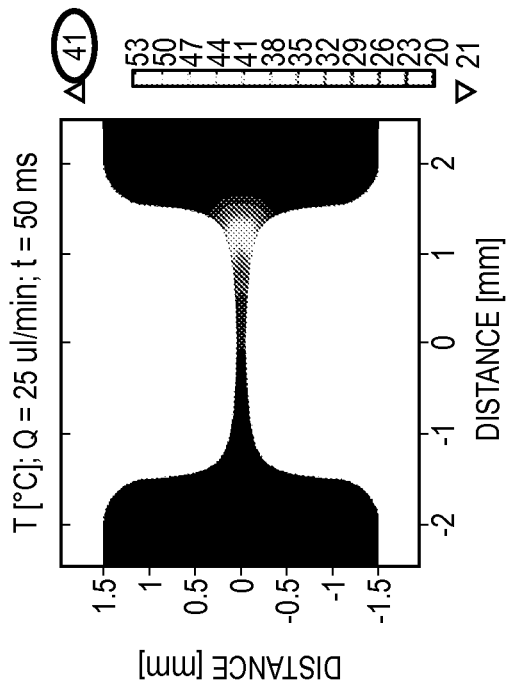
FIGS. 18A-18D are computational results of temperature distributions immediately after and between two 5 ms square pulses (2500 V) delivered at (A) t=0 ms and (D) t=100 ms in 0.01×PBS (σ=0.02 S/m). In the simulation, the flow rate was set to 25 μL/min, and the temperatures plotted at (A) t=5 ms ($1^{st}$ pulse OFF), (B) t=50 ms (between pulses), (C) t=100 ms ($2^{nd}$ pulse ON), and (D) t=105 ms ($2^{nd}$ pulse OFF).
Figure 18B:
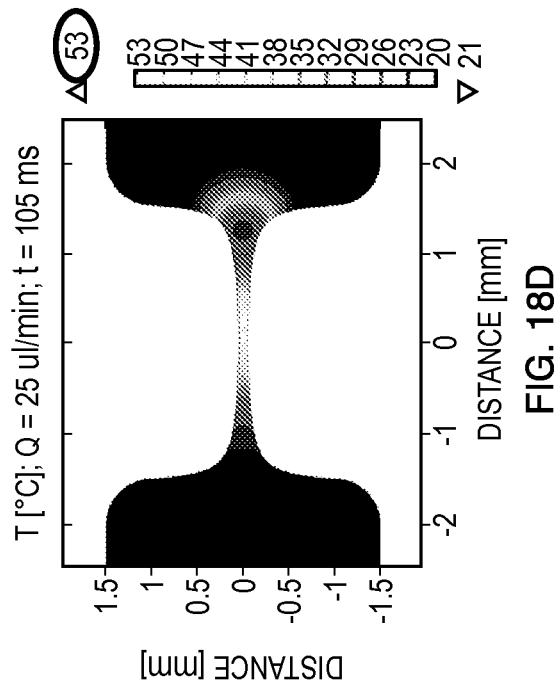
Figure 18C:
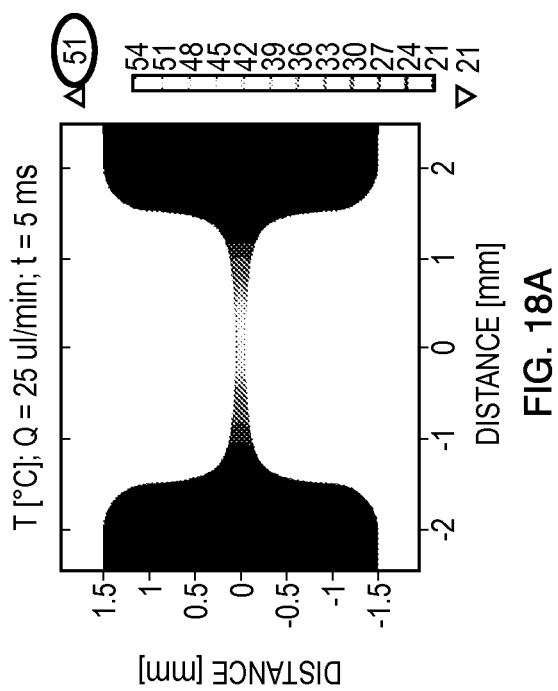
Figure 18D:
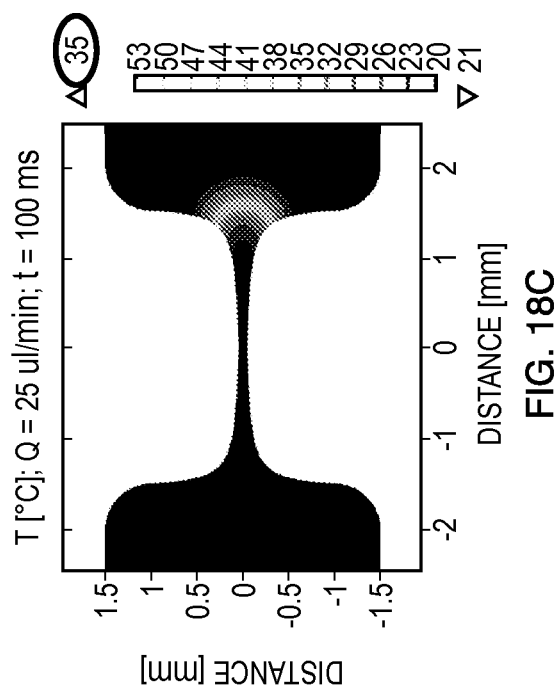

FIGS. 16A-16C present three representative velocity distributions corresponding to flow rates of 25, 50, and 100 µL/min. These results confirm that increasing the flow rate results in higher sample velocities in the microdevice. The effect of flow rate in dissipating the heat generated during the electroporation pulse requires additional numerical models which are outlined below. Specifically, the electric field distribution was simulated for applied voltages of 2000 V, 2500 V, and 3000 V (FIGS. 17A-17C). The resulting electric field distributions confirm that the device may reach electric fields of significant strength to achieve electroporation in plasma membranes of microorganisms and/or mammalian cells. Additionally, from the electric fields and the physical properties of the suspending buffer (0.01×PBS; σ=0.02 S/m), the dissipated energy (e.g., Joule heating, which increases the temperature) was computed for a 5 ms square pulse. It is commonly known that Joule heating is a function of electric field, duration of exposure, and electrical conductivity of the buffer. Therefore, altering those parameters results in different temperature profiles. Nevertheless, these representative examples are provided for illustration of the optimization method of the electromagnetic conditions in a computational manner prior to experimentation.

FIGS. 18-20 summarize the simulated thermal responses for each of the flow rates (25 µL/min, 50 µL/min, 100 µL/min) investigated. Specifically, two 5 ms square pulse delivered at times t=0 ms and t=100 ms, in addition to the heat dissipation, between the pulses was modeled. These experimental scenarios were modeled to evaluate the possibility of cells experiencing multiple pulses if the pulses are delivered without allowing for enough time for the fluid flow to transport the cells outside the constriction region and also remove the heat by convection. In addition, it is important to confirm that the increase in temperature during the pulse delivery will not affect the viability of the cells to maximize transfection efficiency. For different microorganisms and cells it may be necessary to alter the initial temperature of the device to ensure that Joule heating does not result in temperatures that compromise cell viability.

Optimal electromagnetic conditions for electroporation may rely on exposing the cells to multiple pulses. Therefore, additional constriction regions may be designed and fabricated in series (e.g., downstream) in order to expose the cells to the desired electromagnetic conditions. Additionally, the individual constriction regions may have independent geometries that may be specifically designed to induce electroporation (e.g., high electric field) and/or electrokinetically facilitate transport of the exogenous agent (e.g., low electric field for electrophoresis and/or dielectrophoresis). For example, one constriction region capable of achieving electroporation may be followed by at least one constriction region that is designed for transporting the nucleic acid or protein into the cell interior. Finally, several combinations of the high voltage and low voltage sequences may be designed for specific cells in order to improve transfection efficiency or macromolecule delivery.

FIGS. 18A-18D present temperature results that demonstrate that a flow rate of 25 µL/min may be insufficient to dissipate the thermal effects before the delivery of a second pulse for this particularly channel geometry. Specifically, when t=50 ms, there is still a significant band of cells exposed to the electric fields that previously reached a maximum temperature of 51° C. at t=5 ms. Additionally, the temperature distribution at t=105 ms demonstrates that there is some thermal overlap which suggests that a sub-population of the cells exposed to the electric fields experienced multiple pulses. In situations where the increased temperature is beneficial for electroporation, such flow conditions could be used to enhance electroporation.

Figure 19A:
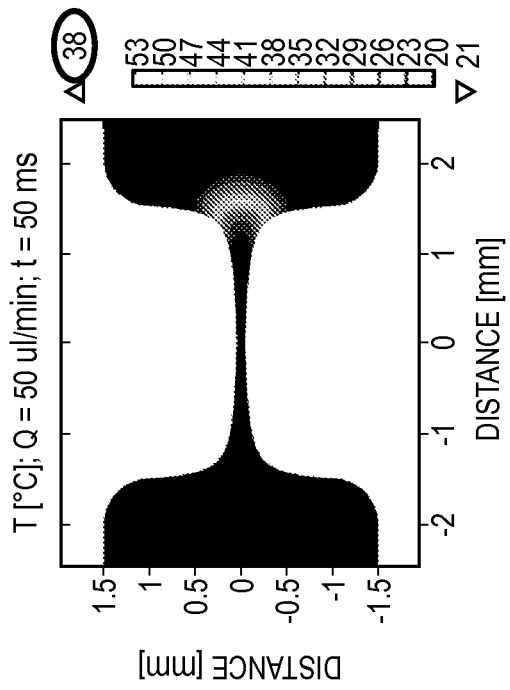
FIGS. 19A-19D are computational results of temperature distributions immediately after and between two 5 ms square pulses (2500 V) delivered at (A) t=0 ms and (D) t=100 ms in 0.01×PBS (σ=0.02 S/m). In the simulation, the flow rate was set to 50 μL/min, and the temperatures plotted at (A) t=5 ms ($1^{st}$ pulse OFF), B) t=50 ms (between pulses), (C) t=100 ms ($2^{nd}$ pulse ON), and (D) t=105 ms ($2^{nd}$ pulse OFF).
Figure 19B:
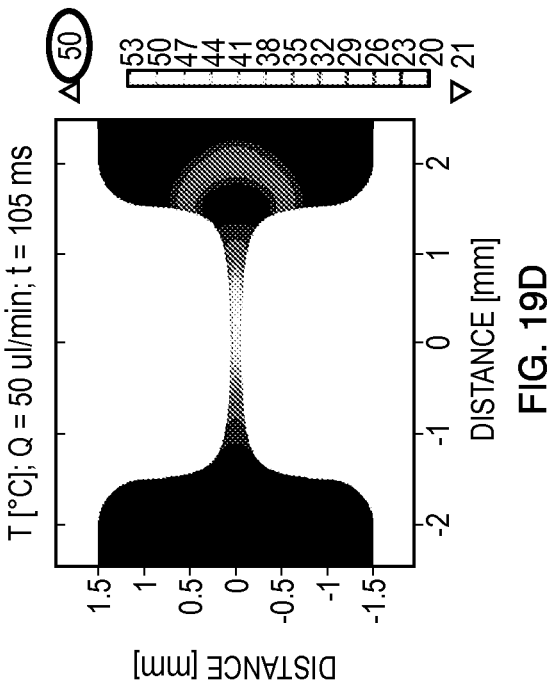
Figure 19C:
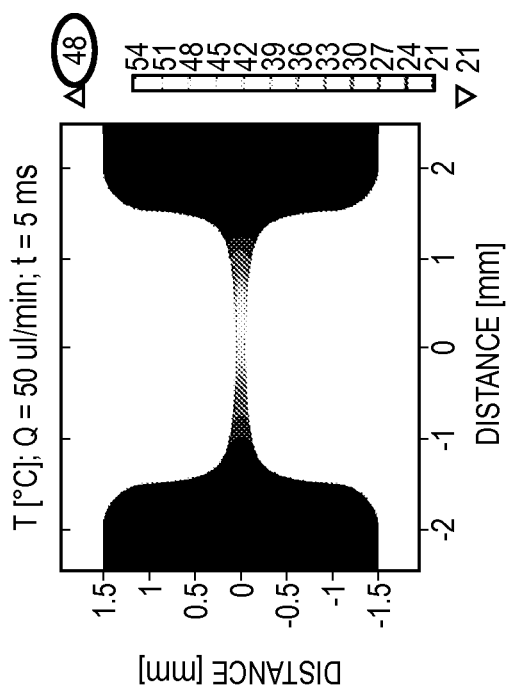
Figure 19D:
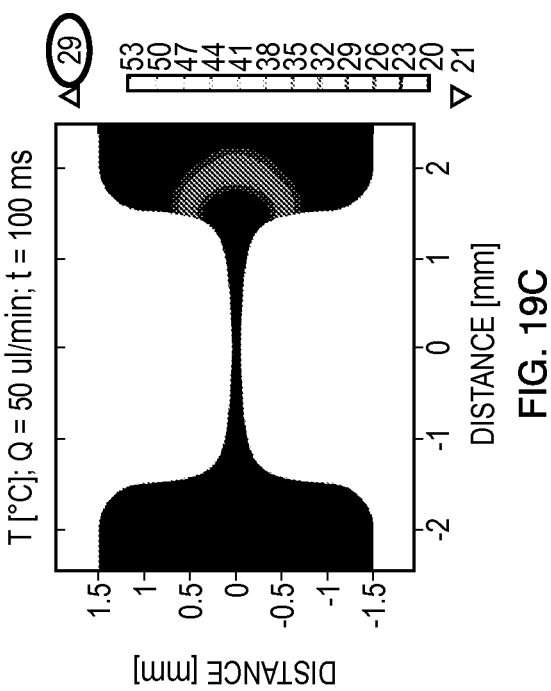

FIGS. 19A-19D demonstrate that a flow rate of 50 µL/min may be optimal for dissipating the heat entirely from the constriction region before the delivery of the second pulse (t=100 ms). At t=50 ms (FIG. 19B) there may not be sufficient time for dissipation of the thermal energy deposited within the constriction region. However, FIG. 19C provides numerical results that corroborate the initial simulation estimates reported in Table 2, demonstrating that 100 ms is sufficient to transport the cells outside the constriction region and remove the heat generated during the electroporation pulse before the onset of the following pulse.

Figure 20A:
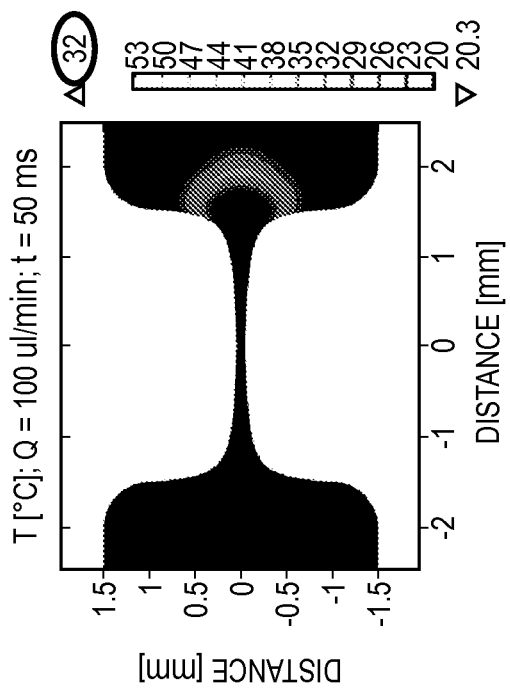
FIGS. 20A-20D are computational results of temperature distributions immediately after and between two 5 ms square pulses (2500 V) delivered at (A) t=0 ms and (D) t=100 ms in 0.01×PBS (σ=0.02 S/m). In the simulation, the flow rate was set to 100 μL/min, and the temperatures plotted at (A) t=5 ms ($1^{st}$ pulse OFF), (B) t=50 ms (between pulses), (C) t=100 ms ($2^{nd}$ pulse ON), and (D) t=105 ms ($2^{nd}$ pulse OFF).
Figure 20B:
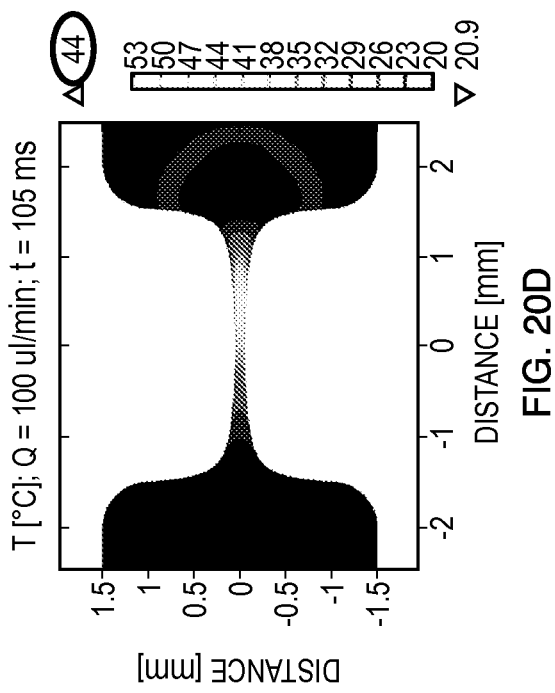
Figure 20C:
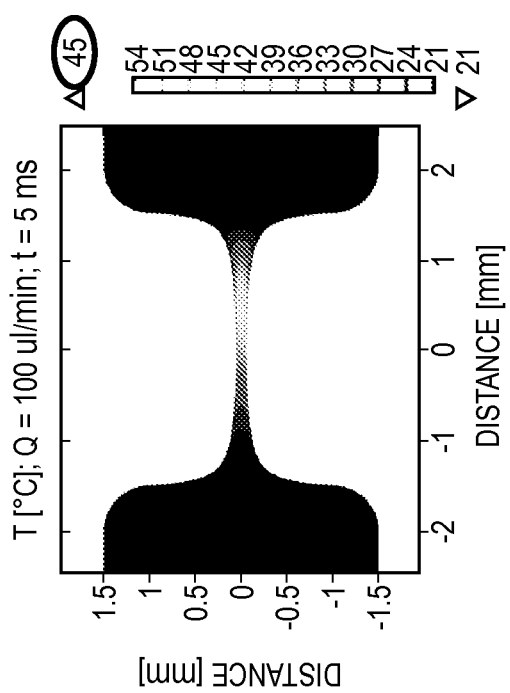
Figure 20D:
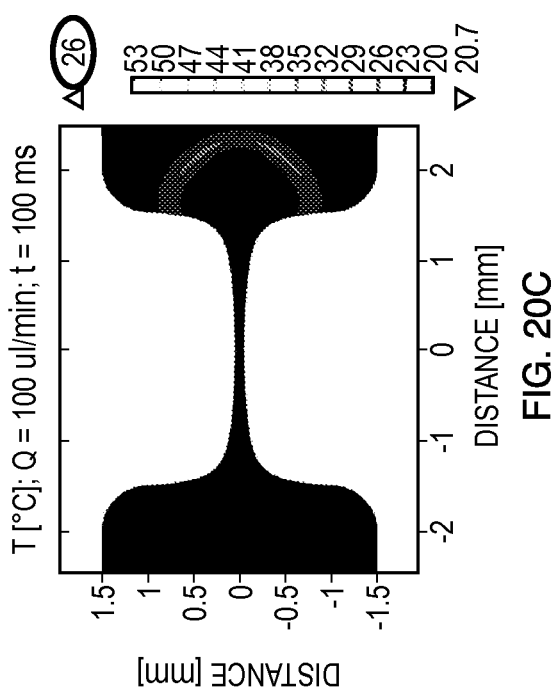

FIGS. 20A-20D indicate that a flow rate of 100 µL/min appears to have achieved sufficient heat dissipation of the thermal energy even by t=50 ms (FIG. 20B). This results in a significant spatial separation between the samples exposed to the electric fields during the first and second pulses (FIG. 20D) that would result in a subpopulation of cells not being exposed to the electric field, reducing the efficiency of the electroporation process. A flow rate of 100 µL/min also results in a lower $T_{max}$ at the completion of the second pulse ($T_{max}$=44° C.) in comparison with the first pulse ($T_{max}$=45° C.) but exposes the cells to a broader range of electric fields for the given electromagnetic conditions explored.

Figures 21A, 21B:
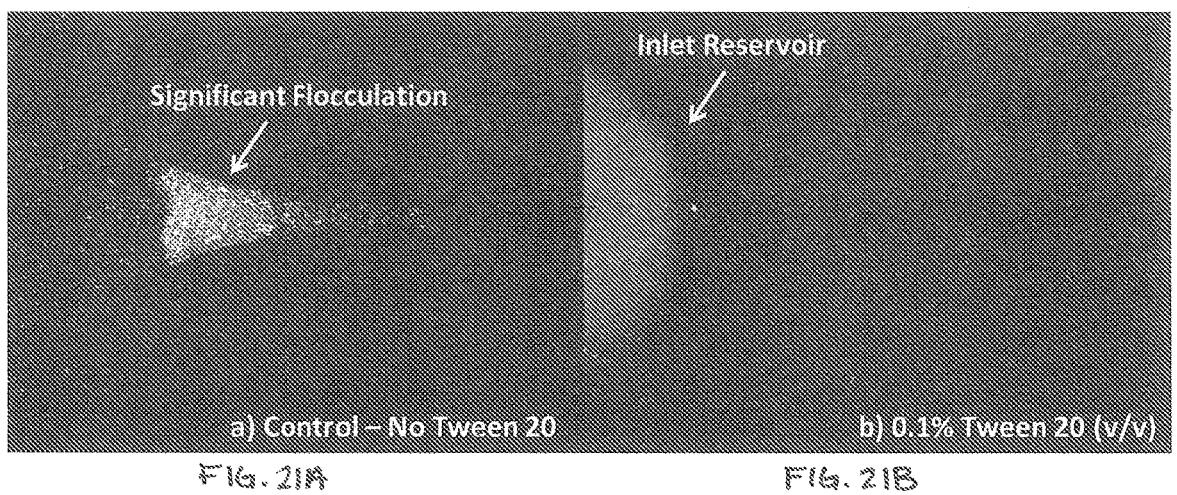
FIG. 21A is a representation of cell flocculation in an experimental study.
FIG. 21B is a representation of the resolution of cell flocculation with the addition of Tween™ 20 in an experimental study.

The ability of some cells to flocculate and prevent flow in the channel may also impact the transfection efficiency. To mitigate this behavior, the addition of a surfactant, such as Tween 20 (Sigma-Aldrich, St. Louis, Mo.) may be added to the background media at 0, 0.025, 0.05, 0.1, 0.2, 0.4% (v/v), or other suitably small concentrations. FIG. 21 shows the results of an experiment utilizing *Yarrowia lipolitica* as a model organism on which the cell solution was administered at a flow rate of 50 µl/min and the flocculation behavior was captured in 100-ms intervals. FIG. 21 demonstrates the immediate flocculation behavior that some cells have when in physical contact to the channel walls and to each other without surfactant. By adding the surfactant to the cell solution, cell flocculation was significantly mitigated with increasing concentration and was not visually apparent by the 0.1% (v/v) Tween™ 20 concentration. These results are useful for optimization of electroporation conditions since cell flocculation can prevent efficient genetic transformation as well.

Embodiments of the device of the present invention may be fabricated by several techniques including soft lithography techniques 2200, such as those as shown in FIGS. 22A-22D. Photo masks 2215 may be designed and optimized in traditional computer aided design (CAD) software and printed. Features of the device may then be patterned on a silicon wafer 2210 using a photoresist material 2225, for example SU-8 2015 Permanent Epoxy Negative Photoresist (Micro-Chem, Westborough, Mass.). The photoresist material may be coated onto the silicon wafer to achieve a thickness corresponding to the desired channel height of the device, for example, 15 µm, in order to focus the field of view relatively close to the bacteria dimensions (about 2 µm). The photoresist material may then be covered by photo mask 2215 and a glass slide 2220 prior to being cured by exposure to UV light 2230 (FIG. 22A). Following exposure, an exposed region results in a master 2235 for the device. The wafer 2210 may then be exposed to a developer to dissolve regions not exposed to the UV light 2230 (FIG. 22B). The master may then be coated with a polymer 2240, such as polydimethylsiloxane (PDMS) and cured. The master 2235 is then removed and the polymer device 2240 may be bonded to a glass slide 2245. More detailed procedures are described by Geng et al. (Geng, T., et al., "Transfection of cells using flow-through electroporation based on constant voltage," *Nat. Protocols,* 2011. 6(8): p. 1192-1208), the relevant teachings of which are incorporated herein by reference.

Figure 23A:
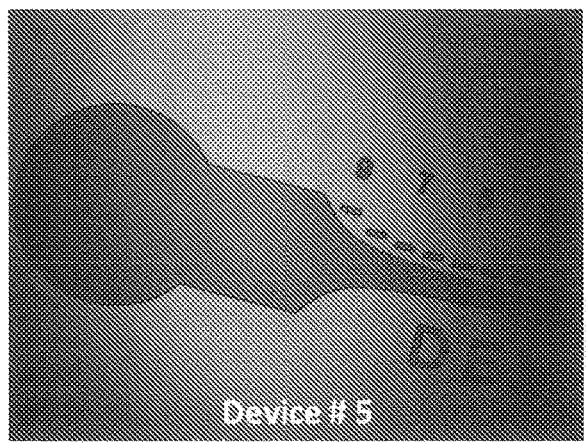
FIGS. 23A-23B are representations of the design of an embodiment of an apparatus described herein.
Figure 23B:
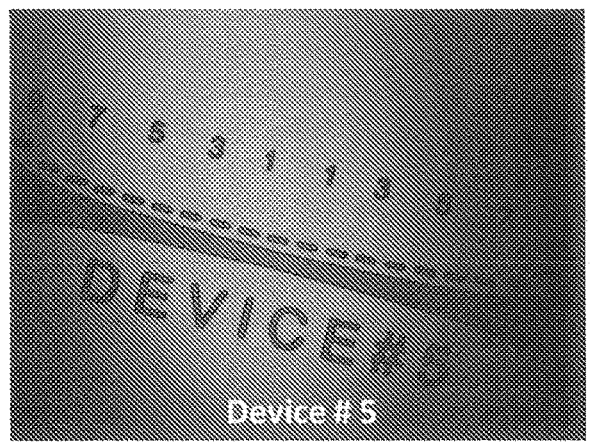

Representative images of device design of embodiment 600 of the invention are shown in FIG. 23. Features of these devices include labeling of each geometry and numbered scale bars outside the constriction region for assisting in locating the transition zone of electroporation due to uptake of the fluorescent dye for post-processing purposes.

As demonstrated in FIGS. 16-20, utilizing embodiment 1000 of the present application allows electroporation within the constriction region by exposing cells to a subset of the continuous electric field spectrum. However, there may be therapeutic or biotechnology applications in which it is desired to expose cells to and broader or entire spectrum of continuous electric fields. In this case, a cell suspension may be driven through the channel at a constant volumetric flow rate, and the cells may be exposed to a constant applied voltage for the entirety of their residence in the channel. In order to satisfy mass conservation, the flow speed $v_{avg}$ must vary with position along the channel:

$$v_{avg}(x) = \frac{Q}{A(x)}, \quad (4)$$

where Q is the (constant) volumetric flow rate and A(x) is the position-dependent cross-sectional area of the channel. FIG. 24B plots $v_{avg}$ as a function of x for a typical value of Q=50 μL/min.

Figure 24A:
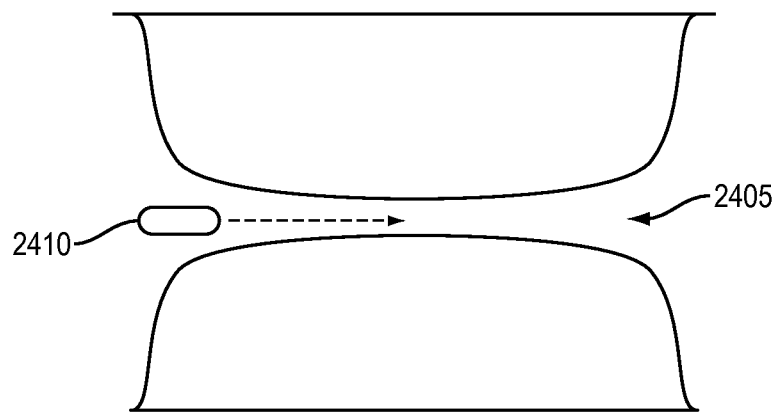
FIG. 24A is a schematic of a bacterial cell moving in a constricted microchannel.
Figure 24B:
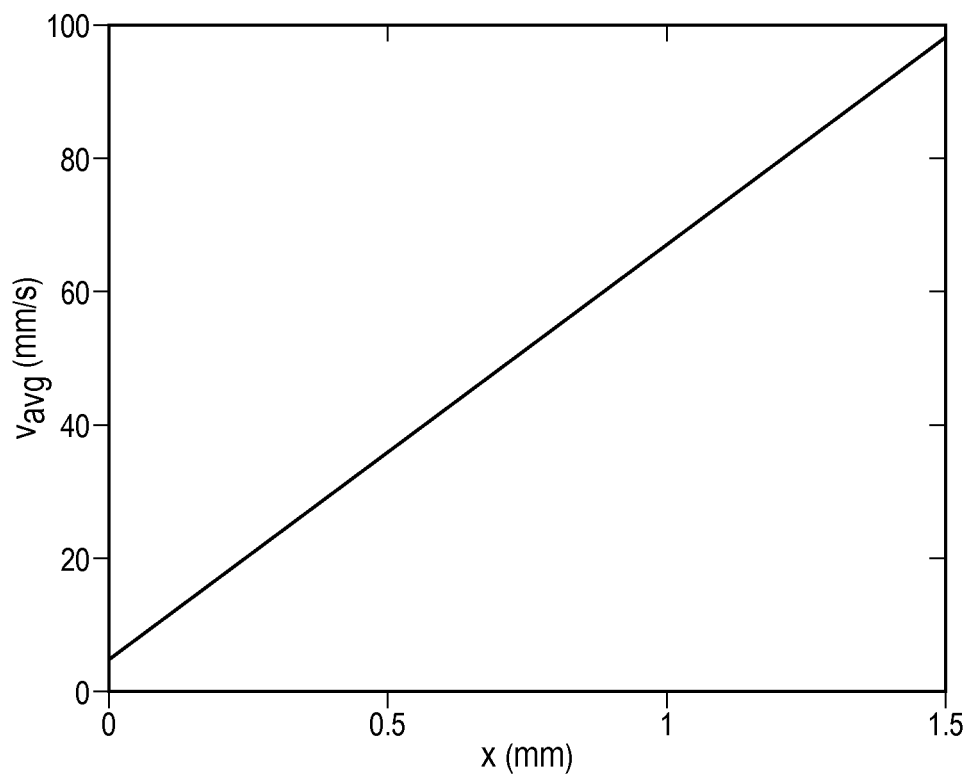
FIG. 24B is a representation of an area-average fluid velocity along the journey of the cell depicted in FIG. 24A, which may be approximately equal to the translational speed of a cell as it is carried through the channel by a flow. To satisfy mass conservation, the fluid, and thus the cells, must accelerate as the microchannel constricts and decelerate as the microchannel expands. In this case, the volume flow rate is set to 50 μL/min.
Figure 25C:
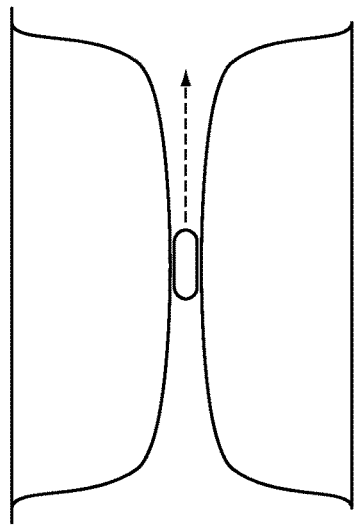
FIG. 25C is a schematic of a bacterial cell moving in a constricted microchannel. The cell begins at the narrowest point of the constriction region and moves toward the widest point.
Figure 25D:
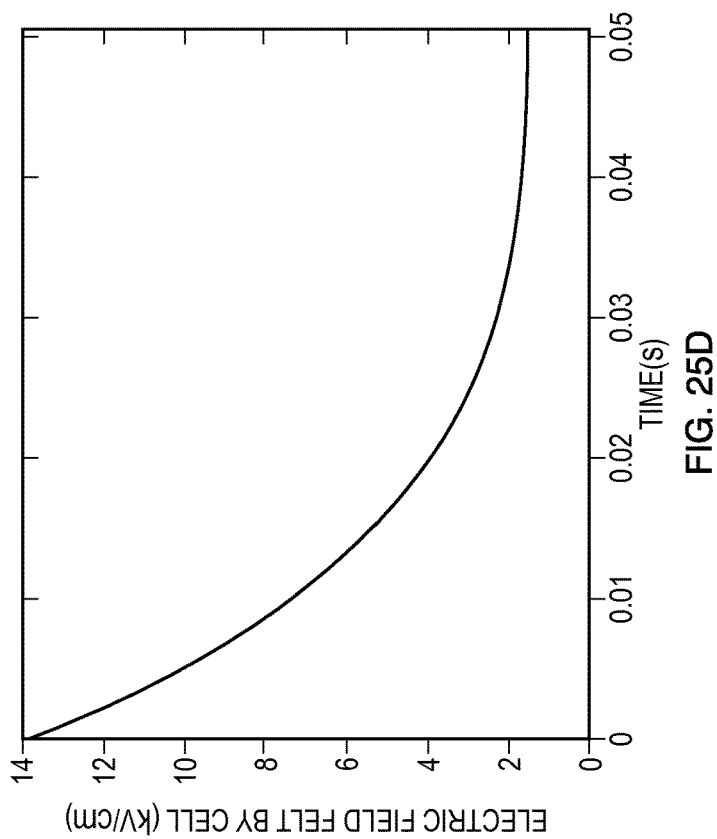
FIG. 25D is the electric field magnitude experienced by the bacterial cell of FIG. 25C as a function of time (also known as, "Lagrangian electric field"). Due to the cell's motion in non-uniform velocity and electric fields, the electric field felt by the cell follows a unique "waveform" dictated by the shape of the channel. As in FIG. 24, the volume flow rate is set to 50 µL/min.
Figure 25A:
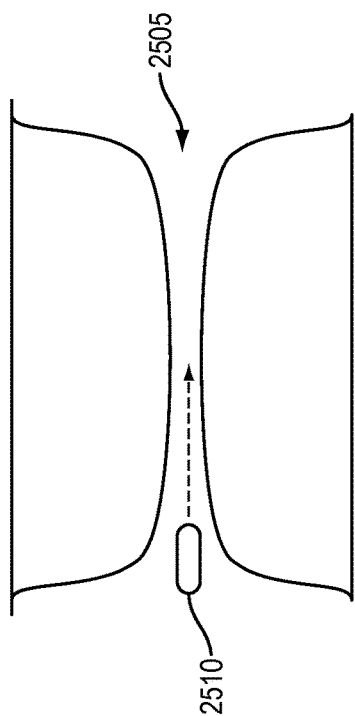
FIG. 25A is a schematic of a bacterial cell moving in a constricted microchannel. The cell begins its journey at the widest point of the constriction region and moves toward the narrowest point.
Figure 25B:
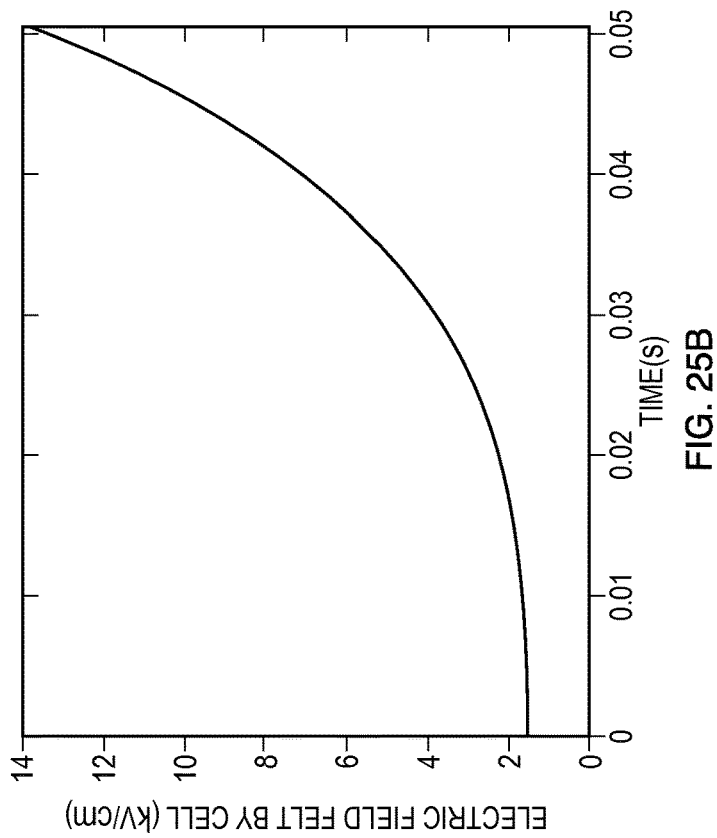
FIG. 25B is the electric field magnitude experienced by the bacterial cell of FIG. 25A as a function of time (also known as, "Lagrangian electric field").

FIG. 24B is a representation of an area-average fluid velocity along the journey of the cell depicted in FIG. 24A, which may be approximately equal to the translational speed of a cell as it is carried through the channel by a flow. To satisfy mass conservation, the fluid, and thus the cells, must accelerate as the microchannel constricts and decelerate as the microchannel expands. In this case, the volume flow rate is set to 50 μL/min.

FIGS. 25A-D show a numerical calculation of the electric field experienced by a cell 2510 as a function of time as the cell moves through a constricted microchannel 2505. Since in this case the cell 2510 is moving through a non-uniform electric field, the electric field strength experienced by the cell (the so-called "Lagrangian measurement" of electric field) will vary with time at a rate that is proportional to its speed and to the local spatial gradient of electric field. Mathematically, this principle is expressed using the material derivative. The time rate of change of electric field from the cell's perspective is given as $$\left.\frac{dE}{dt}\right|_{cell} = v_{avg}\frac{\partial E}{\partial x}, \quad (5)$$

where $v_{avg}$ is the area-average fluid velocity in the flow (x-) direction and $$\frac{\partial E}{\partial x}$$

is the local gradient in electric field. Due to the cell's motion in the non-uniform velocity and electric fields, the practice of flow-through electroporation utilizing embodiment 1000 of the device exposes the cells to unique "waveforms" that are dictated by the shape of the constriction region. Embodiments of the present invention thus provide the novel ability to design customized pulse waveforms, which may yield superior transfection results for certain species, by specifying a cross-sectional area of the constriction region that varies along the flow direction and adjusting the flow-rate.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for cell electroporation, the apparatus comprising:
   a structure comprising a constriction region having a volume defining a cross-sectional area that constricts with a curved geometry, wherein the constriction region is at least 2 mm long, wherein the structure is configured to contain cells having a plasma membrane and background media, the background media including an exogenous agent capable of translocating across a plasma membrane in an electroporated state; and
   an arrangement of electrodes arranged relative to the structure to produce levels of an electromagnetic field, at least one of the levels sufficient to electroporate at least a subset of the plasma membranes in at least a portion of the volume, the exogenous agent responsively translocating across at least some of the subset of the plasma membranes in the electroporated state into cells.

2. The apparatus of claim 1, wherein the volume is symmetric about a central axis.

3. The apparatus of claim 1, wherein the curved geometry results in a linear electromagnetic field gradient within the volume.

4. The apparatus of claim 1, wherein the electrodes are configured to produce an electromagnetic field having a magnitude of at least about 0.5 kV/cm.

5. The apparatus of claim 1, wherein the electrodes are configured to produce an electromagnetic field having a magnitude of about 18 kV/cm and a pulse duration of about 1.0 ms.

6. The apparatus of claim 1, wherein the electrodes are configured to produce an electromagnetic field having a magnitude of about 1.0 kV/cm and a pulse duration of about 10 ms.

7. The apparatus of claim 1, wherein the volume is a flow path configured to contain cells travelling at a flow rate and the electrodes are configured to produce an electromagnetic field having a magnitude of at least about 1.0 kV/cm for a flow rate of about 5.0 μL/min to about 100 μL/min.

8. The apparatus of claim 1, wherein the curved geometry results in a non-linear electromagnetic field gradient within the volume.

9. The apparatus of claim 1, wherein the arrangement of electrodes includes at least one electrode positioned at an inlet port of the volume and at least another electrode positioned at an outlet port of the volume.

* * * * *